US012357557B2

(12) United States Patent
Liard

(10) Patent No.: US 12,357,557 B2

(45) Date of Patent: Jul. 15, 2025

(54) COMPOSITION COMPRISING A (POLY)CARBODIIMIDE COMPOUND AND A COLORING AGENT

(71) Applicant: L'OREAL, Paris (FR)

(72) Inventor: Alexis Liard, Saint-Ouen (FR)

(73) Assignee: L'OREAL, Paris (FR)

( * ) Notice: Subject to any disclaimer, the term of this patent is extended or adjusted under 35 U.S.C. 154(b) by 555 days.

(21) Appl. No.: 17/778,352

(22) PCT Filed: Nov. 19, 2020

(86) PCT No.: PCT/EP2020/082777

§ 371 (c)(1),
(2) Date: May 19, 2022

(87) PCT Pub. No.: WO2021/099517

PCT Pub. Date: May 27, 2021

(65) Prior Publication Data

US 2023/0087090 A1 Mar. 23, 2023

(30) Foreign Application Priority Data

Nov. 21, 2019 (FR) ...................................... 1913059

(51) Int. Cl.

| | |
|---|---|
| ***A61Q 5/10*** | (2006.01) |
| ***A61K 8/19*** | (2006.01) |
| ***A61K 8/81*** | (2006.01) |
| ***A61K 8/88*** | (2006.01) |
| ***A61K 8/898*** | (2006.01) |

(52) U.S. Cl.

CPC .................. *A61K 8/88* (2013.01); *A61K 8/19* (2013.01); *A61K 8/8147* (2013.01); *A61K 8/898* (2013.01); *A61Q 5/10* (2013.01); *A61K 2800/432* (2013.01)

(58) Field of Classification Search

CPC .......... A61K 8/88; A61K 8/19; A61K 8/8147; A61K 8/898; A61K 2800/432; A61K 8/40; A61K 8/8152; A61K 8/84; A61K 8/87; A61Q 5/10; A61Q 5/065

USPC .............................................................. 8/405

See application file for complete search history.

(56) References Cited

U.S. PATENT DOCUMENTS

| | | | | |
|---|---|---|---|---|
| 3,412,054 | A | 11/1968 | Milligan et al. | |
| 4,185,087 | A | 1/1980 | Morlino | |
| 4,284,730 | A | 8/1981 | Narayan et al. | |
| 4,578,266 | A | 3/1986 | Tietjen et al. | |
| 4,957,732 | A | 9/1990 | Grollier et al. | |
| 5,645,609 | A | 7/1997 | Andrean et al. | |
| 7,445,770 | B2 | 11/2008 | Berezkin et al. | |
| 7,452,770 | B2 | 11/2008 | Shea | |
| 2008/0269352 | A1 | 10/2008 | Falkowski et al. | |
| 2010/0183536 | A1 | 7/2010 | Ansmann et al. | |
| 2017/0189311 | A1* | 7/2017 | Macneill | A61K 8/88 |
| 2017/0189312 | A1* | 7/2017 | Van Nguyen | A61K 8/40 |
| 2018/0371237 | A1 | 12/2018 | Tsukamoto et al. | |
| 2019/0001163 | A1* | 1/2019 | Rughani | A61K 8/84 |

FOREIGN PATENT DOCUMENTS

| | | | | |
|---|---|---|---|---|
| CA | 2509861 | A1 | 12/2005 | |
| EP | 0186507 | A2 | 7/1986 | |
| EP | 0342834 | A2 | 11/1989 | |
| EP | 0530974 | A1 | 3/1993 | |
| EP | 0714954 | A2 | 6/1996 | |
| EP | 1184426 | A2 | 3/2002 | |
| FR | 2679771 | A1 | 2/1993 | |
| JP | 05-017710 | A | 1/1993 | |
| JP | 07-258460 | A | 10/1995 | |
| JP | 09-188830 | A | 7/1997 | |
| JP | 10-158450 | A | 6/1998 | |
| JP | 10-158541 | A | 6/1998 | |
| JP | 2002-187932 | A | 7/2002 | |
| JP | 2019504048 | A * | 2/2019 | A61Q 5/02 |
| KR | 10-1453218 | B1 | 10/2014 | |
| WO | 95/01772 | A1 | 1/1995 | |
| WO | 95/15144 | A1 | 6/1995 | |
| WO | 2007/068371 | A1 | 6/2007 | |
| WO | 2008/155059 | A2 | 12/2008 | |
| WO | 2016/084971 | A1 | 6/2016 | |
| WO | WO 2017117522 | A1 * | 7/2017 | A61Q 5/02 |
| WO | 2018/079774 | A1 | 5/2018 | |
| WO | WO 2019006331 | A1 * | 1/2019 | A61Q 5/10 |
| WO | 2019/211050 | A1 | 11/2019 | |
| WO | 2021/099515 | A1 | 5/2021 | |

OTHER PUBLICATIONS

STIC Search Report dated Feb. 20, 2025.*

International Search Report and Written Opinion for counterpart Application No. PCT/EP2020/082777, dated Mar. 11, 2021.

International Search Report and Written Opinion for counterpart Application No. PCT/EP2020/082775, dated Feb. 23, 2021.

Derksen, A.J., "Polycarbodiimides as Classification-Free and Easy to Use Crosslinkers for Water-Based Coatings," XP055719203, Jul. 8, 2017, Retrieved from the Internet: https://web.archive.org/web/20170708064027/https://www.pcimag.com/ext/resources/WhitePapers/2017/Stahl-Polymers-White-paper-PolyCarbodiimide-Crosslinkers.pdf [retrieved on Jul. 30, 2020], the whole document.

Todd, Charles, et al., "Volatile Silicone Fluids for Cosmetic Formulations," Cosmetics and Toiletries, vol. 91, Jan. 1976, pp. 29-32.

Schlossman, Mitchell L., "Treated Pigments New Ways to Impart Color on the Skin," Cosmetics and Toiletries, vol. 105, Feb. 1990, pp. 53-64.

Non-Final Office Action for co-pending U.S. Appl. No. 17/778,353, dated Jun. 3, 2025.

* cited by examiner

*Primary Examiner* — Eisa B Elhilo

(74) *Attorney, Agent, or Firm* — THE MARBURY LAW GROUP, PLLC

(57) ABSTRACT

The present invention relates to a composition (C) for the treatment of keratin fibers, comprising at least one (poly) carbodiimide compound chosen from the compounds of formula (I), and at least one coloring agent chosen from pigments, direct dyes, and mixtures thereof.

20 Claims, No Drawings

COMPOSITION COMPRISING A (POLY)CARBODIIMIDE COMPOUND AND A COLORING AGENT

CROSS REFERENCE TO RELATED APPLICATIONS

This is a national stage application of PCT/EP2020/082777, filed internationally on Nov. 19, 2020, which claims priority to French Application No. 1913059, filed on Nov. 21, 2019, which are incorporated by reference herein in their entireties.

The present invention relates to a composition (C) for the treatment of keratin fibers, comprising at least one (poly) carbodiimide compound chosen from the compounds of formula (I), and at least one coloring agent chosen from pigments, direct dyes, and mixtures thereof.

The present invention also relates to a process for treating keratin fibers.

TECHNICAL FIELD

In the field of dyeing keratin fibers, in particular human keratin fibers, it is already known practice to dye keratin fibers via various techniques using direct dyes or pigments for non-permanent dyeing, or dye precursors for permanent dyeing.

There are essentially three types of process for dyeing the hair:

a) "permanent" dyeing, the function of which is to afford a substantial modification to the natural color and which uses oxidation dyes which penetrate into the hair fiber and forms the dye via an oxidative condensation process;

b) non-permanent, semi-permanent or direct dyeing, which does not use the oxidative condensation process and withstands four or five shampoo washes; it consists in dyeing keratin fibers with dye compositions containing direct dyes.

c) temporary dyeing, which gives rise to a modification of the natural color of the hair that remains from one shampoo washing to the next, and which serves to enhance or correct a shade that has already been obtained. It may also be likened to a "makeup" process.

For this last type of dyeing, it is known practice to use colored polymers formed by grafting one or more dyes of azo, triphenylmethane, azine, indoamine or anthraquinone nature onto a polymer chain. These colored polymers are not entirely satisfactory, notably as regards the homogeneity of the coloring obtained and its resistance, not to mention the problems associated with their manufacture and notably with their reproducibility.

Another dyeing method consists in using pigments. Specifically, the use of pigment on the surface of keratin fibers generally makes it possible to obtain visible colorings on dark hair, since the surface pigment masks the natural color of the fiber. However, the colorings obtained via this dyeing method have the drawback of having poor resistance to shampoo washing and also to external agents such as sebum, perspiration, blow-drying and/or rubbing.

In addition, compositions for temporarily dyeing the hair may also lead to a hair feel that is uncosmetic and/or not natural; the hair thus dyed may notably lack softness and/or suppleness and/or strand separation.

In addition, there are no effective makeup-removing compositions for removing this type of temporary dye composition when it is persistent with respect to shampoo washing.

The need thus remains for a composition for treating keratin fibers, notably the hair, which has the advantage of obtaining a homogeneous and smooth colored coating on the hair, and also hair with complete strand separation, while at the same time forming a coating that is persistent with respect to shampoo washing and to the various attacking factors to which the hair may be subjected, such as blow-drying and/or rubbing, without degrading the hair. There is also a need to be able to eliminate this colored coating when so desired.

Thus, the aim of the present invention is to develop a composition for treating keratin fibers, notably the hair, which has the advantage of obtaining a homogeneous and smooth colored coating on the hair, and also hair with complete strand separation, while at the same time forming a coating that is persistent with respect to shampoo washing and to the various attacking factors to which the hair may be subjected, such as blow-drying and/or rubbing, without degrading the hair. Advantageously, the colored coating can be readily eliminated when so desired.

DISCLOSURE OF THE INVENTION

One subject of the present invention is thus a composition (C) for the treatment of keratin fibers, comprising:

a) at least one (poly)carbodiimide compound chosen from the compounds of formula (I) as defined below, and b) at least one coloring agent chosen from pigments, direct dyes, and mixtures thereof.

The present invention also relates to a process for cosmetically treating, in particular dyeing, keratin fibers such as the hair, in which composition (C) as defined above is applied to said fibers.

Through the use of this composition (C) on keratin fibers, colored coatings are obtained on the hair that make it possible to obtain a coloring that is visible on all types of hair in a manner that is persistent with respect to shampoo washing, while at the same time preserving the physical qualities of the keratin fibers. Such a coating may be resistant to the external attacking factors to which the hair may be subjected, such as blow-drying and perspiration. It makes it possible in particular to obtain a smooth and uniform deposit.

Moreover, this composition makes it possible to obtain hair with perfect strand separation, which can be styled without problem and which has good cosmetic properties, notably in terms of softness and feel.

Advantageously, the colored coating thus obtained can be readily eliminated by means of a makeup-removing composition.

The term "hair with strand separation" means hair which, after application of the composition and drying, is not stuck together (or of which all the strands are separated from each other) and thus does not form clumps of hair.

For the purposes of the present invention, the term "coloring that is persistent with respect to shampoo washing" means that the coloring obtained persists after one shampoo wash, preferably after three shampoo washes, more preferentially after five shampoo washes.

The term "keratin fibers" particularly means human keratin fibers such as head hair, eyelashes, eyebrows, and bodily hair, preferentially head hair, eyebrows and eyelashes, even more preferentially head hair.

The term "at least one" means one or more.

The invention is not limited to the illustrated examples. The features of the various examples may notably be combined within variants which are not illustrated.

For the purposes of the invention and unless otherwise indicated:

an "alkyl" radical denotes a saturated linear or saturated branched hydrocarbon-based radical containing from 1 to 24 carbon atoms, particularly from 1 to 20 carbon atoms, more particularly from 1 to 12 carbon atoms, preferably of $C_1$-$C_6$, even more preferentially of $C_2$-$C_4$. For example, the alkyl group represents a methyl, an ethyl, a propyl, an isopropyl, a butyl, an isobutyl, a tert-butyl, a pentyl, an isopentyl, a hexyl, an isohexyl, a heptyl, an octyl, a nonyl or a decyl; preferably methyl, ethyl or propyl;

an "aminoalkyl" radical denotes an alkyl radical as defined previously, said alkyl radical comprising an $NH_2$ group;

a "hydroxyalkyl" radical denotes an alkyl radical as defined previously, said alkyl radical comprising an OH group;

an "alkylene" radical denotes a divalent alkyl group with "alkyl" as defined previously, preferentially of $C_2$-$C_4$, linear or branched, such as methylene, ethylene or propylene;

a "cycloalkyl" or "alicycloalkyl" radical denotes a cyclic saturated monocyclic or bicyclic, preferably monocyclic, hydrocarbon-based group comprising from 1 to 3 rings, preferably 2 rings, and comprising from 3 to 24 carbon atoms, in particular comprising from 3 to 20 carbon atoms, more particularly from 3 to 13 carbon atoms, even more particularly from 3 to 12 carbon atoms, preferably between 5 and 10 carbon atoms, such as cyclopropyl, cyclopentyl, cyclohexyl, cycloheptyl or norbornyl, in particular cyclopropyl, cyclopentyl or cyclohexyl, it being understood that the cycloalkyl radical may be substituted with one or more ($C_1$-$C_4$) alkyl groups such as methyl; preferably, the cycloalkyl group is then an isobornyl group, a "cycloalkylene" radical denotes a divalent cycloalkyl group with "cycloalkyl" as defined previously, preferably of $C_3$-$C_{12}$;

an "aryl" radical is a monocyclic, bicyclic or tricyclic, fused or non-fused, unsaturated and aromatic hydrocarbon-based cyclic radical, comprising from 6 to 14 carbon atoms, preferably between 6 and 12 carbon atoms; preferably, the aryl group comprises 1 ring of 6 carbon atoms such as phenyl, naphthyl, anthryl, phenanthryl and by phenyl, it being understood that the aryl radical may be substituted with one or more ($C_1$-$C_4$)alkyl groups such as methyl, preferably tolyl, xylyl, or methylnaphthyl; preferably, the aryl group represents phenyl;

an "arylene" radical is a divalent aryl radical with "aryl" as defined previously; preferably, arylene represents phenylene;

a "heterocyclic" radical denotes a saturated or unsaturated, non-aromatic or aromatic, monocyclic or polycyclic hydrocarbon-based radical, comprising one or more heteroatoms, preferably from 1 to 5 atoms chosen from O, S or N, including from 3 to 20 ring members, preferably between 5 and 10 ring members, such as imidazolyl, pyrrolyl and furanyl;

a "heterocycloalkylene" radical is a divalent heterocyclic group with "heterocyclic" as defined previously;

an "aryloxy" radical denotes an aryl-oxy or aryl-O radical with "aryl" as defined previously;

an "alkoxy" radical denotes an alkyl-oxy or alkyl-O— radical with "alkyl" as defined previously;

an "acyloxy" radical denotes an ester radical R—C(O)—O— with R being an alkyl group as defined previously.

Composition (C) according to the invention is preferably a composition for dyeing keratin fibers such as the hair.

(Poly)Carbodiimide Compound:

Composition (C) according to the invention comprises at least one (poly)carbodiimide compound chosen from the compounds of formula (I) below:

[Chem. 1]

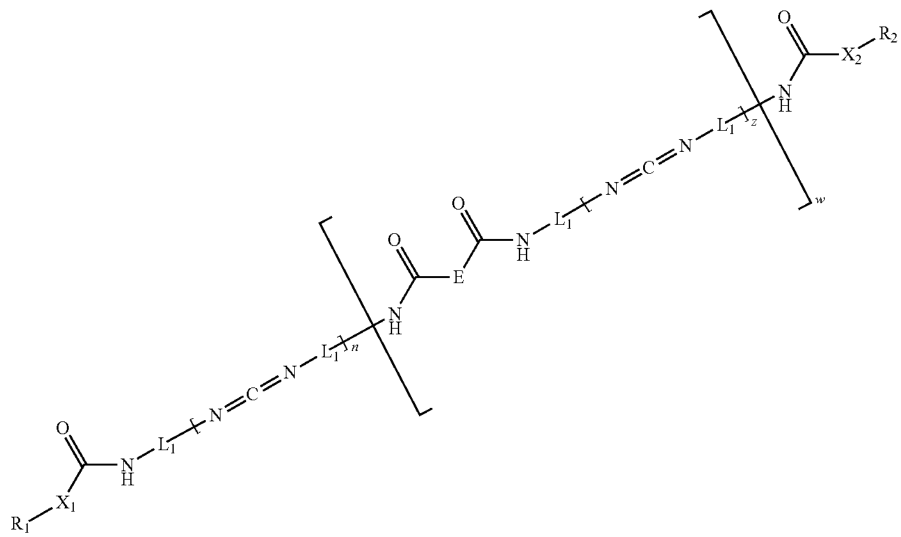

(I)

in which formula (I):

$X_1$ and $X_2$ independently represent an oxygen atom O, a sulfur atom S or an NH group;

$R_1$ and $R_2$ independently represent a hydrocarbon-based radical optionally interrupted with one or more heteroatoms, n and z denote an integer ranging from 1 to 20, with $n+z \geq 2$ and w denotes an integer ranging from 1 to 3;

$L_1$ independently represents a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof;

E independently represents a group chosen from:

$—O—R_3—O—$; $—S—R_4—S—$; $—R_5—N(R_6)—R_4—N(R_6)—R_5—$;

in which $R_3$ and $R_4$ independently represent a divalent hydrocarbon-based radical optionally interrupted with one or more heteroatoms;

$R_5$ independently represents a covalent bond or a saturated divalent hydrocarbon-based radical, optionally interrupted with one or more heteroatoms;

$R_6$ independently represents a hydrogen atom or a hydrocarbon-based radical, optionally interrupted with one or more heteroatoms.

The composition may comprise at least two different (poly)carbodiimide compounds, present as a mixture in the composition.

The term "(poly)carbodiimide compound" means a compound comprising one or more carbodiimide groups, preferably at least two carbodiimide groups, more preferentially at least three carbodiimide groups; in particular, the number of carbodiimide groups does not exceed 200, preferably 150, more preferentially 100.

The term "carbodiimide group" means a linear triatomic fraction of general formula $—(N{=}C{=}N)—$.

The term "hydrocarbon-based radical" means a saturated or unsaturated, linear or branched radical containing from 1 to 300 carbon atoms, preferably from 1 to 250 carbon atoms, more preferentially from 1 to 200 carbon atoms. Preferably, the hydrocarbon-based radical is a saturated linear radical.

The hydrocarbon-based radical may comprise one or more cyclic groups.

The hydrocarbon-based radical may be interrupted with one or more heteroatoms, in particular chosen from O, S or N and/or substituted with one or more cations, anions or zwitterions or cationic groups such as ammonium, anionic groups such as carboxylate, or zwitterionic groups, and/or comprising a metal ion which may be incorporated in the form of a salt.

The term "heteroatom(s)" means an oxygen O, sulfur S or nitrogen N atom, and also halogen atoms such as Cl, F, Br and I. If the heteroatom is included in the chain of the hydrocarbon-based radical, the heteroatom is preferably chosen from oxygen O, sulfur S or nitrogen N atoms.

Preferably, $X_1$ and $X_2$ independently represent an oxygen atom.

Preferably, $R_1$ and $R_2$ are independently chosen from dialkylamino alcohols, alkyl esters of hydroxycarboxylic acid and monoalkyl ethers of (poly)alkylene glycol, in which a hydroxyl group has been removed, and mixtures thereof.

In a preferred embodiment, $R_1$ and $R_2$ are independently chosen from groups (i) to (iv) below:

(i) the compound of formula (II) below:

[Chem.2]

$$R_7—O—C(O)—C(R_8)(H)— \quad (II)$$

in which $R_7$ represents a $C_1$-$C_3$alkyl group and $R_8$ represents a hydrogen atom or a $C_1$-$C_3$ alkyl group; preferably, $R_7$ is a methyl and $R_8$ is a hydrogen atom or a methyl.

(ii) the compound of formula (III) below:

[Chem.3]

$$R_9—[O—CH_2—C(H)(R_{10})]_p— \quad (III)$$

in which $R_9$ represents a $C_1$-$C_4$alkyl group, $R_{10}$ represents a hydrogen atom or a $C_1$-$C_4$ alkyl group and p denotes an integer ranging from 1 to 3; preferably, $R_9$ is a methyl, ethyl or butyl, $R_{10}$ is a hydrogen atom or a methyl and p is equal to 1.

(iii) the compound of formula (IV) below:

[Chem.4]

$$(R_{11})_2N—CH_2—C(H)(R_{12})— \quad (IV)$$

in which $R_{11}$ represents a $C_1$-$C_4$alkyl group and $R_{12}$ represents a hydrogen atom or a $C_1$-$C_4$ alkyl group; preferably, $R_{11}$ is a methyl, ethyl or butyl and $R_{12}$ is a hydrogen atom or a methyl.

(iv) the compound of formula (V) below:

[Chem.5]

$$R_{13}—[O—CH_2—C(H)(R_{14})]_q— \quad (V)$$

in which $R_{13}$ represents a $C_1$-$C_4$alkyl group or a phenyl, $R_{14}$ represents a hydrogen atom or a $C_1$-$C_4$ alkyl group and q denotes an integer ranging from 4 to 30; preferably, $R_{13}$ is a methyl, ethyl or butyl and $R_{14}$ is a hydrogen atom or a methyl.

Preferably, $R_1$ and $R_2$ independently represent a compound of formula (V) in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30.

According to an alternative embodiment, $R_1$ and $R_2$ are different and one of the radicals $R_1$ or $R_2$ represents a compound of formula (III) as described above and the other radical $R_1$ or $R_2$ represents a compound of formula (V) as described above.

Preferably, in formula (III), $R_9$ is a methyl, ethyl or butyl and $R_{10}$ is a hydrogen atom or a methyl and p is equal to 1.

Preferably, in formula (V), $R_{13}$ is a methyl, ethyl or butyl and $R_{14}$ is a hydrogen atom or a methyl and q denotes an integer ranging from 4 to 30.

According to another alternative embodiment, $R_1$ and $R_2$ are identical and represent a compound of formula (V) in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30.

Preferably, n is an integer ranging from 1 to 20, more preferentially from 2 to 20.

Preferably, z denotes an integer ranging from 1 to 20, more preferentially from 2 to 20.

Preferably, w is equal to 1.

Preferably, w is equal to 1, n+z denotes an integer ranging from 4 to 10.

Preferably, $L_1$ is chosen from a $C_1$-$C_{18}$ divalent aliphatic hydrocarbon-based radical such as methylene, ethylene and propylene, a $C_3$-$C_{15}$ cycloalkylene radical such as cyclopentylene, cycloheptylene and cyclohexylene, a $C_3$-$C_{12}$ heterocycloalkylene group such as imidazolene, pyrrolene and furanylene, or a $C_6$-$C_{14}$ arylene group such as phenylene, and mixtures thereof.

For example, $L_1$ may be chosen from a radical derived from tolylene diisocyanate, hexamethylene diisocyanate, xylylene diisocyanate, 2,2,4-trimethylhexamethylene diisocyanate, 1,12-dodecane diisocyanate, norbornane diisocyanate, 2,4-bis(8-isocyanatooctyl)-1,3-dioctylcyclobutane, 4,4'-dicylclohexylmethane diisocyanate, tetramethylxylylene diisocyanate, isophorone diisocyanate, 1,5-napththylene diisocyanate, 4,4'-diphenylmethane diisocyanate, 4,4'-diphenyldimethylmethane diisocyanate and phenylene diisocyanate, and mixtures thereof.

Preferably, $L_1$ is chosen from a $C_3$-$C_{15}$ cycloalkylene radical or a $C_6$-$C_{14}$ arylene group, and mixtures thereof, such as the compounds of formula (VI) below:

[Chem. 6]

(VI)

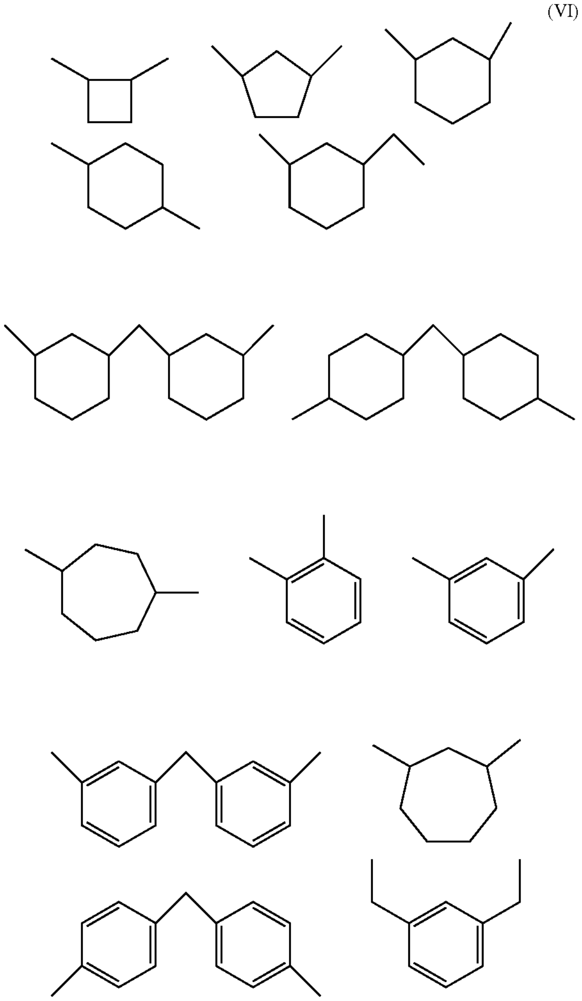

Preferably, $L_1$ is 4,4-dicyclohexylenemethane corresponding to formula (VII) below:

[Chem. 7]

(VII)

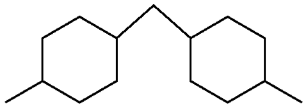

According to another embodiment, when $L_1$ is a $C_6$-$C_{14}$ arylene group, $L_1$ is not the m-tetramethylxylylene radical represented by formula (VIII) below:

[Chem. 8]

(VIII)

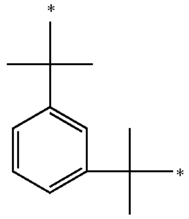

As indicated previously, E independently represents a group chosen from:

—O—$R_3$—O—; —S—$R_4$—S—; —$R_5$—N($R_6$)—$R_4$—N($R_6$)—$R_5$—;

in which $R_3$ and $R_4$ independently represent a divalent hydrocarbon-based radical optionally interrupted with one or more heteroatoms;

$R_5$ independently represents a covalent bond or a saturated divalent hydrocarbon-based radical, optionally interrupted with one or more heteroatoms; and $R_6$ independently represents a hydrogen atom or a hydrocarbon-based radical, optionally interrupted with one or more heteroatoms.

Preferably, $R_3$ and $R_4$ are independently chosen from a $C_6$-$C_{14}$ arylene radical such as phenylene, a $C_3$-$C_{12}$ cycloalkylene radical such as cyclopropylene and cyclobutylene, a linear or branched $C_1$-$C_{18}$ alkylene radical such as methylene and ethylene, optionally interrupted with one or more heteroatoms, and mixtures thereof.

More preferentially, $R_3$ and $R_4$ are independently chosen from a linear or branched $C_1$-$C_{18}$ alkylene radical such as methylene, butylene, propylene or ethylene, optionally interrupted with one or more heteroatoms.

Preferably, when $R_5$ is not a covalent bond, $R_5$ is chosen from a $C_6$-$C_{14}$ arylene radical such as phenylene, a $C_3$-$C_{12}$ cycloalkylene radical such as cyclopropylene and cyclobutylene, a linear or branched $C_1$-$C_{18}$ alkylene radical such as methylene and ethylene, optionally interrupted with one or more heteroatoms, and mixtures thereof.

Preferably, $R_6$ is chosen from a $C_6$-$C_{14}$ arylene radical such as phenylene, a $C_3$-$C_{12}$ cycloalkylene radical such as cyclopropylene and cyclobutylene, a linear or branched $C_1$-$C_{18}$ alkylene radical such as methylene and ethylene, optionally interrupted with one or more heteroatoms, and mixtures thereof.

Preferably, E represents a group —O—$R_3$—O— in which $R_3$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

More preferentially, E represents a group- —O—$R_3$—O— in which $R_3$ represents a linear or branched $C_1$-$C_{18}$ alkylene radical such as methylene, butylene, propylene or ethylene, optionally interrupted with one or more heteroatoms.

According to a particular embodiment, the (poly)carbodiimide compound is a copolymer derived from α-methylstyryl isocyanates of formula (IX) below:

[Chem. 9]

(IX)

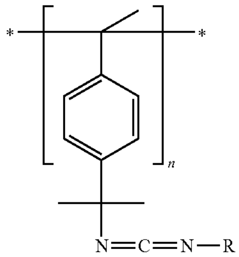

in which R independently represents an alkyl group containing from 1 to 24 carbon atoms, a cycloalkyl group containing from 3 to 24 carbon atoms or an aryl group containing from 6 to 24 carbon atoms, and n denotes an integer ranging from 2 to 100.

In this embodiment, the term "alkyl group" is as defined previously.

In this embodiment, the term "cycloalkyl group" is as defined previously.

In this embodiment, n may denote an integer ranging from 2 to 50, preferably from 3 to 30 and even more preferentially from 5 to 10.

According to another particular embodiment, the (poly) carbodiimide compound is a compound of formula (X) below:

[Chem. 10]

(X)

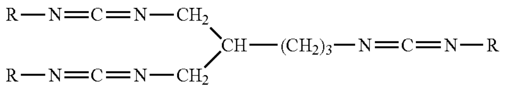

in which R independently represents an alkyl group containing from 1 to 24 carbon atoms, a cycloalkyl group containing from 3 to 24 carbon atoms or an aryl group containing from 6 to 24 carbon atoms.

The alkyl group, the cycloalkyl group and the aryl group are as defined previously.

Preferably, the (poly)carbodiimide compound is chosen from the compounds of formula (I) in which:

- $X_1$ and $X_2$ independently represent an oxygen atom;
- $R_1$ and $R_2$, are independently chosen from dialkylamino alcohols, alkyl esters of hydroxycarboxylic acid and monoalkyl ethers of (poly)alkylene glycol, in which a hydroxyl group has been removed, and mixtures thereof;
- n and z denote an integer ranging from 1 to 20, with n+z≥2 and w is equal to 1;
- $L_1$ is chosen from a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof;
- E independently represents a group chosen from:
- —O—$R_3$—O—; —S—$R_4$—S—; —$R_5$—N($R_6$)—$R_4$—N($R_6$)—$R_5$—;

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof;

- when $R_5$ is not a covalent bond, $R_5$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof; and
- $R_6$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

More preferentially, the (poly)carbodiimide compound is chosen from the compounds of formula (I) in which:

- $X_1$ and $X_2$ independently represent an oxygen atom;
- $R_1$ and $R_2$ are independently monoalkyl ethers of (poly) alkylene glycol, in which a hydroxyl group has been removed;
- n and z denote an integer ranging from 1 to 20, with n+z≥2 and w is equal to 1;
- $L_1$ is a $C_3$-$C_{15}$ cycloalkylene radical;
- E independently represents a group chosen from:
- —O—$R_3$—O—; —S—$R_4$—S—; —$R_5$—N($R_6$)—$R_4$—N($R_6$)—$R_5$—;

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof;

- when $R_5$ is not a covalent bond, $R_5$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof; and
- $R_6$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

Even more preferentially, the (poly)carbodiimide compound is chosen from the compounds of formula (I) in which:

- $X_1$ and $X_2$ independently represent an oxygen atom;
- $R_1$ and $R_2$ independently represent the compound of formula (V) below:

[Chem.11]

$$R_{13}—[O—CH_2—C(H)(R_{14})]_q— \quad (V)$$

in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30;

- n and z denote an integer ranging from 2 to 20, with n+z ranging from 4 to 10 and w is equal to 1;
- $L_1$ is a $C_3$-$C_{15}$ cycloalkylene radical such as cyclopentylene, cycloheptylene, cyclohexylene and 4,4-dicyclohexylenemethane; and
- E represents a group —O—$R_3$—O— in which $R_3$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

Even more preferentially, the (poly)carbodiimide compound is chosen from the compounds of formula (I) in which:

$X_1$ and $X_2$ independently represent an oxygen atom;

$R_1$ and $R_2$ independently represent the compound of formula (V) below:

[Chem.12]

$$R_{13}—[O—CH_2—C(H)(R_{14})]_q— \quad (V)$$

in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30;

n and z denote an integer ranging from 1 to 20, with n+z ranging from 4 to 10 and w is equal to 1;

$L_1$ is a $C_3$-$C_{15}$ cycloalkylene radical such as cyclopentylene, cycloheptylene, cyclohexylene and 4,4-dicyclohexylenemethane, preferably 4,4-dicyclohexylenemethane; and E represents a group- —O—$R_3$—O— in which $R_3$ represents a linear or branched $C_1$-$C_{18}$ alkylene radical such as methylene, butylene, propylene or ethylene, optionally interrupted with one or more heteroatoms.

According to a preferred embodiment, the (poly)carbodiimide compound is a compound of formula (XI) below:

[Chem. 13]

(XI)

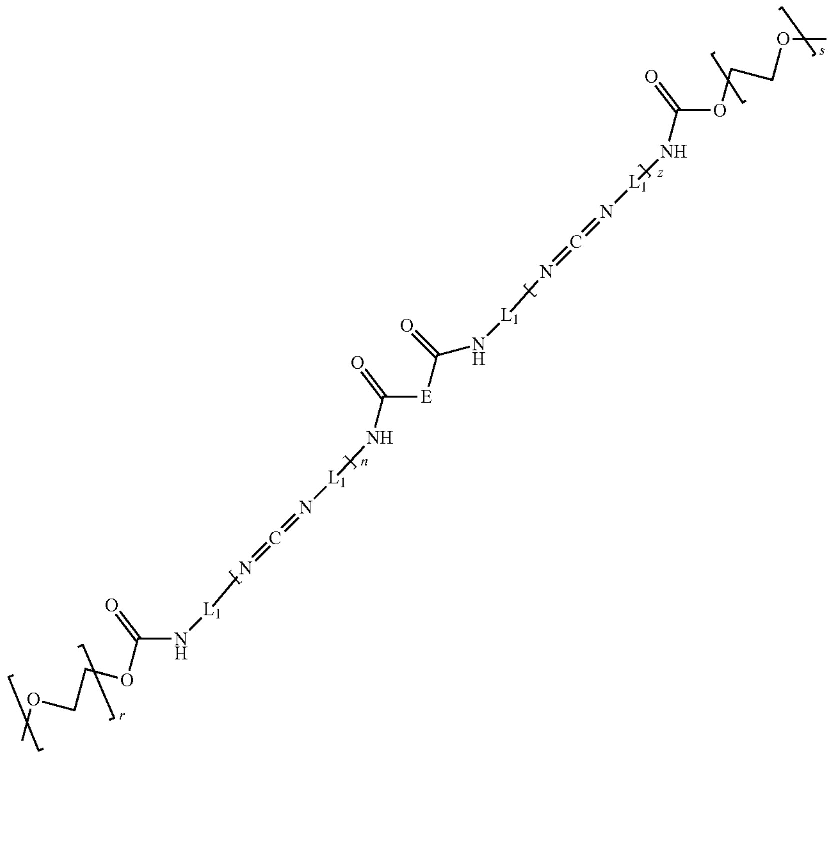

in which $L_1$ is 4,4-dicyclohexylenemethane, n and z denote an integer ranging from 1 to 20, with n+z ranging from 4 to 10, E represents a group —O—$R_3$—O— in which $R_3$ represents a linear or branched $C_1$-$C_{18}$ alkylene radical such as methylene, propylene, butylene or ethylene, optionally interrupted with one or more heteroatoms, and r and s denote an integer ranging from 4 to 30.

The total amount of the (poly)carbodiimide compound(s), present in the composition according to the invention, preferably ranges from 0.01% to 40% by weight, more preferentially from 0.1% to 30% by weight, better still from 0.5% to 25% by weight and even better still from 1% to 10% by weight relative to the total weight of composition (C).

Aqueous Dispersion of Particles of Polymers:

The composition (C) according to the invention may comprise at least one aqueous dispersion of particles of polymer(s) chosen from polyurethanes, acrylic polymers, and mixtures thereof.

Preferably, the composition (C) comprises at least one aqueous dispersion of particles of polymer(s) chosen from polyurethanes, acrylic polymers, and mixtures thereof.

The dispersion(s) may be simple dispersions in the aqueous medium of the cosmetic composition. As a particular case of dispersions, mention may be made of latexes.

The aqueous dispersion(s) of polymer particles may be chosen from aqueous dispersions of polyurethane particles.

More particularly, the polyurethane(s) present in the aqueous dispersions used in the present invention are derived from the reaction of:

a prepolymer of formula (A) below:

[Chem. 14]

(A)

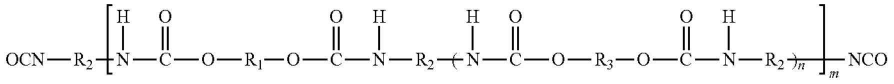

in which:

$R_1$ represents a divalent radical of a dihydroxylated compound, $R_2$ represents a radical of an aliphatic or cycloaliphatic polyisocyanate, $R_3$ represents a radical of a low molecular weight diol, optionally substituted with one or more ionic groups, n represents an integer ranging from 1 to 5, and m is greater than 1;

at least one chain extender according to formula (B) below:

[Chem.15]

$$H_2N—R_4—NH_2 \quad (B)$$

in which $R_4$ represents an alkylene or alkylene oxide radical that is not substituted with one or more ionic or potentially ionic groups; and at least one chain extender according to formula (C) below:

[Chem.16]

$$H_2N—R_5—NH_2 \quad (C),$$

in which $R_5$ represents an alkylene radical substituted with one or more ionic or potentially ionic groups.

Among the dihydroxylated compounds that may be used according to the present invention, mention may be made notably of the compounds containing two hydroxyl groups and having a number-average molecular weight from about 700 to about 16 000, and preferably from about 750 to about 5000. As examples of dihydroxylated compounds of high molecular weight, mention may be made of polyol polyesters, polyol polyethers, polyhydroxylated polycarbonates, polyhydroxylated polyacetates, polyhydroxylated polyacrylates, polyhydroxylated amide polyesters, polyhydroxylated polyalkadienes, polyhydroxylated polythioethers, and mixtures thereof. Preferably, the hydroxylated compounds are chosen from polyol polyesters, polyol polyethers, polyhydroxylated polycarbonates, and mixtures thereof.

The polyisocyanates that may be used according to the present invention are notably chosen from organic diisocyanates with a molecular weight of about 112 to 1000, and preferably about 140 to 400.

Preferably, the polyisocyanates are chosen from diisocyanates and more particularly from those represented by the general formula $R_2(NCO)_2$, in which $R_2$ represents a divalent aliphatic hydrocarbon-based group containing from 4 to 18 carbon atoms, a divalent cycloaliphatic hydrocarbon-based group containing from 5 to 15 carbon atoms, a divalent araliphatic hydrocarbon-based group containing from 7 to 15 carbon atoms or a divalent aromatic hydrocarbon-based group containing from 6 to 15 carbon atoms.

Preferably, $R_2$ represents an organic diisocyanate. As examples of organic diisocyanates, the following may notably be chosen: tetramethylene diisocyanate, 1,6-hexamethylene diisocyanate, dodecamethylene diisocyanate, 1,3-diisocyanatocyclohexane, 1,4-diisocyanatocyclohexane, 3-isocyanatomethyl-3,5,5-trimethylcyclohexane isocyanate (isophorone diisocyanate or IPDI), bis(4-isocyanatocyclohexyl)methane, 1,3-bis(isocyanatomethyl)cyclohexane, 1,4-bis(isocyanatomethyl)cyclohexane, bis(4-isocyanato-3-methyl-cyclohexyl)methane, isomers of toluene diisocyanate (TDI) such as toluene 2,4-diisocyanate, toluene 2,6-diisocyanate and mixtures thereof, hydrogenated toluene diisocyanate, diphenylmethane 4,4'-diisocyanate and mixtures with its diphenylmethane 2,4-diisocyanate isomers and optionally diphenylmethane 2,2'-diisocyanate isomers, naphthalene 1,5-diisocyanate, and mixtures thereof.

Preferably, the diisocyanates are aliphatic and cycloaliphatic diisocyanates, and are more preferentially chosen from 1,6-hexamethylene diisocyanate, 3-isocyanatomethyl-3,5,5-trimethylcyclohexane isocyanate, and mixtures thereof.

According to the present invention, the term “low molecular weight diol” refers to a diol with a molecular weight from about 62 to 700, and preferably from 62 to 200. These diols may comprise aliphatic, alicyclic or aromatic groups. Preferably, they comprise only aliphatic groups.

Preferably, $R_3$ represents a low molecular weight diol containing more than 20 carbon atoms, more preferentially chosen from ethylene glycol, diethylene glycol, 1,2-propanediol, 1,3-propanediol, 1,4-butanediol, 1,3-butylene glycol, neopentyl glycol, butylethylpropanediol, cyclohexanediol, 1,4-cyclohexanedimethanol, 1,6-hexanediol, bisphenol A (2,2-bis(4-hydroxyphenyl)propane), hydrogenated bisphenol A (2,2-bis(4-hydroxycyclohexyl)propane), and mixtures thereof.

The low molecular weight diols may optionally comprise ionic or potentially ionic groups. Examples of low molecular weight diols containing ionic or potentially ionic groups are notably described in U.S. Pat. No. 3,412,054. Such compounds are preferably chosen from dimethylolbutanoic acid, dimethylolpropionic acid, polycaprolactone diols containing a carboxyl group, and mixtures thereof.

If low molecular weight diols containing ionic or potentially ionic groups are used, they are preferably used in an amount such that less than 0.30 meq of COOH per gram of polyurethane is present in the polyurethane dispersion.

The prepolymer is extended by means of two families of chain extenders. The first family of chain extenders corresponds to the compounds of general formula (B).

The chain extenders of formula (B) are preferably chosen from alkylenediamines, such as hydrazine, ethylenediamine, propylenediamine, 1,4-butylenediamine, piperazine; alkylene oxide diamines, such as 3-{2-[2-(3-aminopropoxy)ethoxy]ethoxy}propylamine (also known as dipropylamine diethylene glycol or DPA-DEG available from Tomah Products, Milton, Wis.), 2-methyl-1,5-pentanediamine (Dytec A from DuPont), hexanediamine, isophorone diamine, 4,4- methylenedi(cyclohexylamine), ether-amines of the DPA series, available from Tomah Products, Milton, Wis., such as dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol; and mixtures thereof.

The second family of chain extenders corresponds to the compounds of general formula (C). Such compounds preferably have an ionic or potentially ionic group and two groups that can react with isocyanate groups. Such compounds may optionally comprise two groups that react with isocyanate groups and one group which is ionic or capable of forming an ionic group.

The ionic or potentially ionic group may preferably be chosen from ternary or quaternary ammonium groups or groups that can be converted into such groups, a carboxyl group, a carboxylate group, a sulfonic acid group and a sulfonate group. The at least partial conversion of groups that can be converted into a ternary or quaternary ammonium group salt may be performed before or during the mixing with water.

The chain extenders of formula (C) are preferably chosen from diaminosulfonates, for instance the sodium salt of N-(2-aminoethyl)-2-aminoethanesulfonic acid (ASA), the sodium salt of N-(2-aminoethyl)-2-aminopropionic acid, and mixtures thereof.

The polyurethane that may be used according to the present invention may optionally also comprise compounds which are located, respectively, at the chain ends and terminate said chains (chain terminators). Such compounds are notably described in U.S. Pat. Nos. 7,445,770 and/or 7,452,770.

Preferably, the aqueous dispersion of polyurethane particles has a viscosity of less than 2000 mPa·s at 23° C., more preferentially less than 1500, and even better still less than 1000. Even more preferably, the aqueous polyurethane dispersion has a glass transition temperature of less than 0° C.

Preferably also, the aqueous polyurethane dispersion has a polyurethane (or active material, or solids) content, on the basis of the weight of the dispersion, of from 20% to 60% by weight, more preferentially from 25% to 55% by weight and even better still from 30% to 50% by weight. This means that the polyurethane content (solids) of the aqueous dispersion is preferably from 20% to 60% by weight, more preferentially from 25% to 55% by weight and even better still from 30% to 50% by weight, relative to the total weight of the dispersion.

Preferably also, the aqueous dispersion of polyurethane particles has a glass transition temperature (Tg) of less than or equal to −25° C., preferably less than −35° C. and more preferentially less than −40° C.

The polyurethane particles may have a mean diameter ranging up to about 1000 nm, for example from about 50 nm to about 800 nm, better still from about 100 nm to about 500 nm. These particle sizes may be measured with a laser particle size analyzer (for example Brookhaven BI90).

As nonlimiting examples of aqueous polyurethane dispersions, mention may be made of those sold under the name Baycusan® by Bayer, for instance Baycusan® C1000 (INCI name: polyurethane-34), Baycusan® C1001 (INCI name: polyurethane-34), Baycusan® C1003 (INCI name: polyurethane-32), Baycusan® C1004 (INCI name: polyurethane-35) and Baycusan® C1008 (INCI name: polyurethane-48).

Mention may also be made of the aqueous polyurethane dispersions of isophthalic acid/adipic acid copolymer/hexylene glycol/neopentyl glycol/dimethylol acid/isophorone diisocyanate (INCI name: Polyurethane-1, such as Luviset® PUR, BASF), the polyurethane of polycarbonate, polyurethane and aliphatic polyurethane of aliphatic polyester (such as the Neorez® series, DSM, such as Neorez® R989, Neorez® and R-2202).

According to a preferred embodiment, the aqueous dispersion of polyurethane particles may be chosen from aqueous dispersions of particles of compounds having the INCI name polyurethane-35 or compounds having the INCI name polyurethane-34.

Preferably, the aqueous dispersion(s) of polymers according to the invention are chosen from aqueous dispersions of acrylic polymer particles, and more preferentially from aqueous dispersions of film-forming acrylic polymer particles.

For the purposes of the invention, the term "polymer" means a compound corresponding to the repetition of one or more units (these units being derived from compounds known as monomers). This or these unit(s) are repeated at least twice and preferably at least three times.

The term "film-forming polymer" refers to a polymer that is capable of forming, by itself or in the presence of an auxiliary film-forming agent, a macroscopically continuous film on a support, notably on keratin materials, and preferably a cohesive film.

For the purposes of the present invention, the term "acrylic polymer" means a polymer synthesized from at least one monomer chosen from (meth)acrylic acid and/or (meth)acrylic acid ester and/or (meth)acrylic acid amide.

The unit(s) derived from the (meth)acrylic acid monomers of the polymer may optionally be in the form of salt(s), notably of alkali metal, alkaline-earth metal or ammonium salt(s), or organic base salt(s).

The (meth)acrylic acid esters (also known as (meth)acrylates) are advantageously chosen from alkyl (meth)acrylates, in particular $C_1$ to $C_{30}$, preferably $C_1$ to $C_{20}$ and better still $C_1$ to $C_{10}$ alkyl (meth)acrylates, aryl (meth)acrylates, in particular $C_6$ to $C_{10}$ aryl (meth)acrylates, and hydroxyalkyl (meth)acrylates, in particular $C_2$ to $C_6$ hydroxyalkyl (meth)acrylates.

Among the alkyl (meth)acrylates that may be mentioned are methyl (meth)acrylate, ethyl (meth)acrylate, butyl (meth)acrylate, isobutyl (meth)acrylate, 2-ethylhexyl (meth)acrylate, lauryl (meth)acrylate and cyclohexyl (meth)acrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl(meth)acrylates that may be mentioned are benzyl acrylate and phenyl acrylate.

The (meth)acrylic acid esters that are particularly preferred are alkyl, preferably $C_1$ to $C_{30}$, more preferentially $C_1$ to $C_{20}$, even better still $C_1$ to $C_{10}$, and even more particularly $C_1$ to $C_4$, alkyl (meth)acrylates.

According to the present invention, the alkyl group of the esters may be fluorinated, or even perfluorinated, i.e. some or all of the hydrogen atoms of the alkyl group are substituted with fluorine atoms.

As (meth)acrylic acid amides, examples that may be mentioned include (meth)acrylamides and also N-alkyl (meth)acrylamides, in particular N—($C_2$ to $C_{12}$ alkyl)(meth)acrylamides. Among the N-alkyl(meth)acrylamides that may be mentioned are N-ethylacrylamide, N-t-butylacrylamide, N-t-octylacrylamide and N-undecylacrylamide.

The acrylic polymer according to the invention may be a homopolymer or a copolymer, advantageously a copolymer, better still a copolymer of (meth)acrylic acid and of (meth) acrylic acid esters.

Preferably, the acrylic polymer(s) according to the invention comprise one or more units derived from the following monomers:

a) (meth)acrylic acid; and b) $C_1$ to $C_{30}$, more preferentially $C_1$ to $C_{20}$, better still $C_1$ to $C_{10}$, and even more particularly $C_1$ to $C_4$, alkyl (meth) acrylate.

Preferably, the aqueous dispersion of acrylic polymer particles does not comprise any surfactant.

The term "surfactant" refers to any agent that is capable of modifying the surface tension between two surfaces.

Among the acrylic polymers according to the invention, mention may be made of copolymers of (meth)acrylic acid and of methyl or ethyl (meth)acrylate, in particular copolymers of methacrylic acid and of ethyl acrylate such as the compound sold under the trade name Luvimer MAE by the company BASF, or the compound Polyacrylate-2 Crosspolymer sold under the trade name Fixate Superhold Polymer by the company Lubrizol, or the compound Acrylate Copolymer sold under the trade name Daitosol 3000VP3 by the company Daito Kasei Kogyo, or the compound Acrylate Polymer sold under the trade name Daitosol 3000 SLPN-PE1 by the company Daito Kasei Kogyo.

The acrylic polymer may optionally comprise one or more additional monomers, other than the (meth)acrylic acid and/or (meth)acrylic acid ester and/or (meth)acrylic acid amide monomers.

By way of additional monomer, mention will be made, for example, of styrene monomers, in particular styrene and α-methylstyrene, and preferably styrene.

In particular, the acrylic polymer may be a styrene/(meth) acrylate copolymer and notably a polymer chosen from copolymers resulting from the polymerization of at least one styrene monomer and at least one $C_1$ to $C_{20}$, preferably $C_1$ to $C_{10}$, alkyl (meth)acrylate monomer.

The $C_1$ to $C_{10}$ alkyl (meth)acrylate monomer may be chosen from methyl acrylate, ethyl acrylate, propyl acrylate, butyl acrylate, hexyl acrylate, octyl acrylate and 2-ethylhexyl acrylate.

As acrylic polymer, mention may be made of the styrene/(meth)acrylate copolymers sold under the name Joncryl 77 by the company BASF, under the name Yodosol GH41F by the company Akzo Nobel and under the name Syntran 5760 CG by the company Interpolymer.

Preferably, composition (C) comprises at least one aqueous dispersion of acrylic polymer particles.

More preferentially, composition (C) comprises at least one aqueous dispersion of acrylic polymer particles comprising one or more units derived from the following monomers:

a) (meth)acrylic acid; and b) $C_1$ to $C_{30}$, more preferentially $C_1$ to $C_{20}$, better still $C_1$ to $C_{10}$, and even more particularly $C_1$ to $C_4$, alkyl (meth) acrylate.

Preferably, the aqueous dispersion of acrylic polymer particles has an acrylic polymer (or active material, or solids) content, on the basis of the weight of the dispersion, of from 20% to 60% by weight, more preferentially from 22% to 55% by weight and better still from 25% to 50% by weight.

The total amount of the aqueous dispersion(s) of polymer particles, present in the composition according to the invention, preferably ranges from 0.1% to 40% by weight, more preferentially from 0.1% to 35% by weight and better still from 0.2% to 30% by weight, relative to the total weight of composition (C).

According to a preferred embodiment, the total amount of the aqueous dispersion(s) of acrylic polymer particles, present in the composition according to the invention, preferably ranges from 0.1% to 40% by weight, more preferentially from 0.1% to 35% by weight, and better still from 0.2% to 30% by weight, relative to the total weight of composition (C).

Silicone:

Composition (C) may comprise at least one silicone.

Preferably, composition (C) comprises at least one silicone.

Preferably, composition (C) comprises at least one silicone chosen from non-amino silicones, amino silicones and mixtures thereof.

The silicones may be solid or liquid at 25° C. and atmospheric pressure ($1.013 \times 10^5$ Pa), and volatile or non-volatile.

The silicones that may be used may be soluble or insoluble in the composition according to the invention; they may be in the form of oil, wax, resin or gum; silicone oils are preferred.

Silicones are notably described in detail in Walter Noll's *Chemistry and Technology of Silicones* (1968), Academic Press.

Preferably, the composition contains one or more silicones that are liquid at 25° C. and atmospheric pressure ($1.013 \times 10^5$ Pa).

The volatile silicones may be chosen from those with a boiling point of between 60° C. and 260° C. (at atmospheric pressure) and more particularly from:

i) cyclic polydialkylsiloxanes including from 3 to 7 and preferably 4 to 5 silicon atoms, such as octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia.

cyclocopolymers of the dimethylsiloxane/methylalkylsiloxane type having the chemical structure:

[Chem. 17]

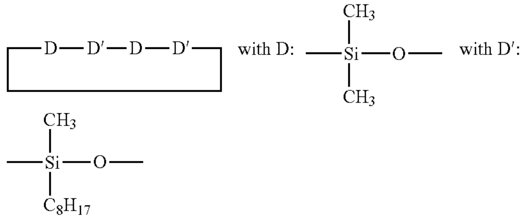

Preferably cyclomethylsiloxane.

Mention may be made of Volatile Silicone FZ 3109 sold by the company Union Carbide.

mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5\times10^{-6}$ $m^2/s$ at 25° C., such as decamethyltetrasiloxane.

Other silicones belonging to this category are described in the article published in Cosmetics and Toiletries, Vol. 91, January 76, pages 27-32, Todd & Byers *Volatile Silicone Fluids for Cosmetics*; mention may be made of the product sold under the name SH 200 by the company Toray Silicone.

Among the nonvolatile silicones, mention may be made, alone or as a mixture, of polydialkylsiloxanes and notably polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups. Preferably, the nonvolatile silicones are chosen from poly dimethyl/methylsiloxanes which are optionally oxyethylenated and oxypropylenated.

The organomodified silicones may be polydiarylsiloxanes, notably polydiphenylsiloxanes, and polyalkylarylsiloxanes, functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:

- polyoxyethylene and/or polyoxypropylene groups optionally including C6-C24 alkyl groups, such as dimethicone copolyols, and notably those sold by the company Dow Corning under the name DC 1248 or the oils Silwet® L 722, L 7500, L 77 and L 711 from the company Union Carbide; or alternatively (C12)alkylmethicone copolyols, and notably those sold by the company Dow Corning under the name Q2 5200;
- substituted or unsubstituted amine groups, in particular C1-C4 aminoalkyl groups; mention may be made of the products sold under the name GP4 Silicone Fluid and GP7100 by the company Genesee, or under the names Q2-8220 and DC929 or DC939 by the company Dow Corning;
- thiol groups, such as the products sold under the names GP 72 A and GP 71 from Genesee;
- alkoxylated groups, such as the product sold under the name Silicone Copolymer F-755 by SWS Silicones and Abil Wax® 2428, 2434 and 2440 by the company Goldschmidt;
- hydroxylated groups, for instance polyorganosiloxanes bearing a hydroxyalkyl function;
- acyloxyalkyl groups, such as the polyorganosiloxanes described in U.S. Pat. No. 4,957,732;
- anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255;
- hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200, with a viscosity of 60 000 $mm^2/s$;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:

- mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning,
- mixtures formed from a polydimethylsiloxane with a hydroxy-terminated chain, or dimethiconol (CTFA), and from a cyclic polydimethylsiloxane, also known as dimethicone (CTFA), such as the product PMX-1503 Fluid sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, mention may be made of the products sold under the following names:

- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH 1000;
- certain oils of the SF series from General Electric, such as SF 1023, SF 1154, SF 1250 and SF 1265.

Preferably, composition (C) comprises at least one amino silicone. The term "amino silicone" denotes any silicone including at least one primary, secondary or tertiary amine or a quaternary ammonium group.

The weight-average molecular masses of these amino silicones may be measured by gel permeation chromatography (GPC) at room temperature (25° C.), as polystyrene equivalent. The columns used are μ styragel columns. The eluent is THF and the flow rate is 1 ml/minute. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

[Chem. 18]

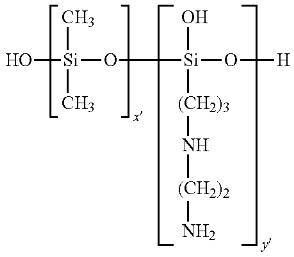

(A)

in which x' and y' are integers such that the weight-average molecular weight (Mw) is between 5000 and 500 000 approximately.

b) the amino silicones corresponding to formula (B):

$R'_aG_{3-a}$-Si$(OSiG_2)_n$-$(OSiG_bR'_{2-b})_m$-O-$SiG_{3-a}$-$R'_a$ (B)

in which:

G, which may be identical or different, denotes a hydrogen atom or a phenyl, OH, $C_1$-$C_8$ alkyl, for example methyl, or $C_1$-$C_8$ alkoxy, for example methoxy, group, a, which may be identical or different, denotes 0 or an integer from 1 to 3, in particular 0, b denotes 0 or 1, in particular 1, m and n are numbers such that the sum (n+m) varies from 1 to 2000 and notably from 50 to 150, it being possible for n to denote a number from 0 to 1999 and in particular from 49 to 149 and it being possible for m to denote a number from 1 to 2000 and in particular from 1 to 10;

R', which may be identical or different, denotes a monovalent radical of formula —CqH2qL in which q is a number ranging from 2 to 8 and L is an optionally quaternized amine group chosen from the following groups: —N(R")2; —N+(R")3 A-; —NR"-Q-N(R")2 and —NR"-Q-N+(R")3 A-, in which R", which may be identical or different, denotes hydrogen, phenyl, benzyl, or a saturated monovalent hydrocarbon-based radical, for example a $C_1$-$C_{20}$ alkyl radical; Q denotes a linear or branched group of formula CrH2r, r being an integer ranging from 2 to 6, preferably from 2 to 4; and A- represents a cosmetically acceptable anion, notably a halide anion such as a fluoride, chloride, bromide or iodide anion.

Preferably, the amino silicone(s) are chosen from the amino silicones of formula (B). Preferably, the amino silicones of formula (B) are chosen from the amino silicones corresponding to formulae (C), (D), (E), (F) and/or (G) below.

According to a first embodiment, the amino silicones corresponding to formula (B) are chosen from the silicones known as “trimethylsilyl amodimethicone” corresponding to formula (C):

[Chem. 19]

(C)

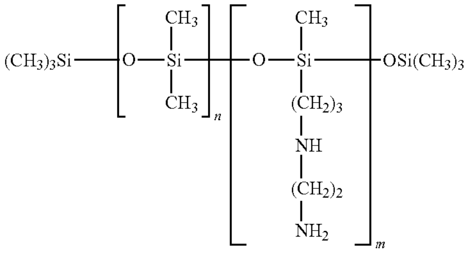

in which m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10.

According to a second embodiment, the amino silicones corresponding to formula (B) are chosen from the silicones of formula (D) below:

[Chem. 20]

(D)

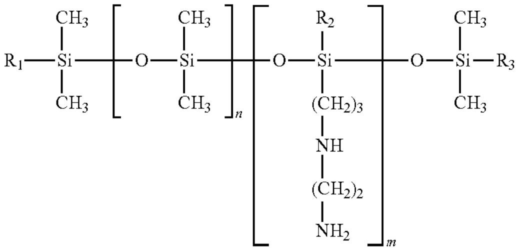

in which:

m and n are numbers such that the sum (n+m) varies from 1 to 1000, notably from 50 to 250 and more particularly from 100 to 200, it being possible for n to denote a number from 0 to 999, in particular from 49 to 249 and more particularly from 125 to 175 and it being possible for m to denote a number from 1 to 1000, in particular from 1 to 10 and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular weight (Mw) of these silicones preferably ranges from 2000 to 1 000 000 and more particularly from 3500 to 200 000.

According to a third embodiment, the amino silicones corresponding to formula (B) are chosen from the silicones of formula (E) below:

[Chem. 21]

(E)

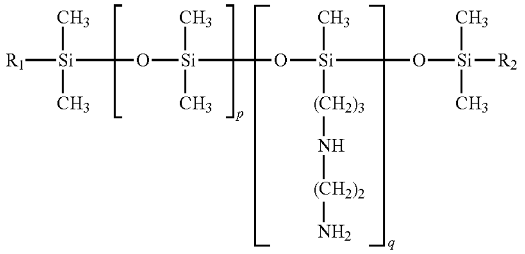

in which:

p and q are numbers such that the sum (p+q) ranges from 1 to 1000, notably from 50 to 350 and more particularly from 150 to 250; p possibly denoting a number from 0 to 999 and in particular from 49 to 349 and more particularly from 159 to 239, and q possibly denoting a number from 1 to 1000, notably from 1 to 10 and more particularly from 1 to 5;

$R_1$ and $R_2$, which may be different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones whose structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300® or Belsil® ADM LOG 1.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-mean size of the silicone particles in the emulsion generally ranges from 3 nm to 500 nanometers. Preferably, notably as amino silicones of formula (E), use is made of microemulsions with a mean particle size ranging from 5 nm to 60 nanometers (limits included) and more particularly from 10 nm to 50 nanometers (limits included). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

[Chem. 22]

(F)

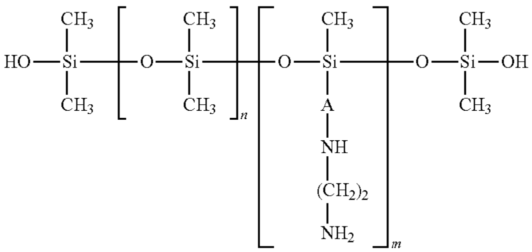

in which:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

Another silicone corresponding to formula (B) is, for example, the Xiameter MEM 8299 Emulsion from Dow Corning (INCI name: amodimethicone and trideceth-6 and cetrimonium chloride).

According to a fifth embodiment, the amino silicones corresponding to formula (B) are chosen from the silicones of formula (G) below:

[Chem. 23]

(G)

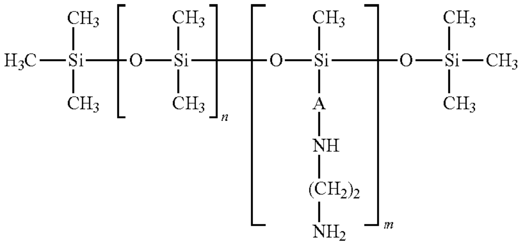

in which:

m and n are numbers such that the sum (n+m) ranges from 1 to 2000 and in particular from 50 to 150, n possibly denoting a number from 0 to 1,999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning;

c) the amino silicones corresponding to the formula (H):

[Chem. 24]

(H)

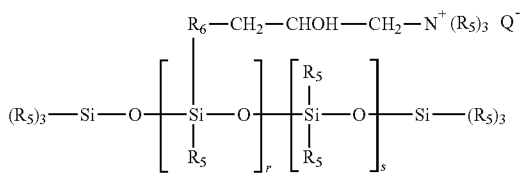

in which:

R5 represents a monovalent hydrocarbon-based radical containing from 1 to 18 carbon atoms, and in particular a C1-C18 alkyl or C2-C18 alkenyl radical, for example methyl;

R6 represents a divalent hydrocarbon-based radical, notably a C1-C18 alkylene radical or a divalent C1-C18, and for example C1-C8, alkylenoxy radical linked to the Si via an SiC bond;

Q- is an anion, such as a halide ion, in particular a chloride ion, or an organic acid salt, in particular an acetate;

r represents a mean statistical value ranging from 2 to 20 and in particular from 2 to 8;

s represents a mean statistical value ranging from 20 to 200 and in particular from 20 to 50.

Such amino silicones are notably described in U.S. Pat. No. 4,185,087.

d) the quaternary ammonium silicones of formula (I):

[Chem. 25]

(I)

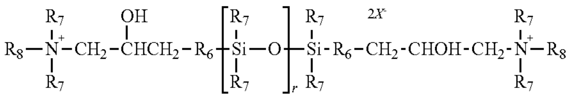

in which:

$R_7$, which may be identical or different, represents a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical linked to the Si via an SiC bond;

R8, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;

X— is an anion, such as a halide ion, in particular a chloride iron, or an organic acid salt, in particular an acetate;

r represents a mean statistical value ranging from 2 to 200 and in particular from 5 to 100.

These silicones are described, for example, in patent application EP-A 0 530 974.

e) the amino silicones of formula (J):

[Chem. 26]

(J)

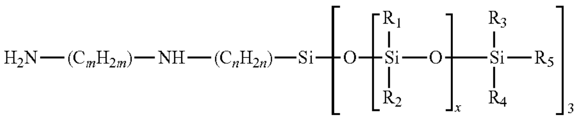

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g.

f) the multiblock polyoxyalkylenated amino silicones of type (AB)n, A being a polysiloxane block and B being a polyoxyalkylene block including at least one amine group.

Said silicones are preferably formed from repeating units having the following general formulae:

$[—(SiMe_2O)_xSiMe_2\text{-}R—N(R'')—R'—O(C_2H_4O)_a(C_3H_6O)_b—R'—N(H)—R—]$ [Chem. 27]

or alternatively $[—(SiMe_2O)xSiMe_2—R—N(R'')—R'—O(C_2H_4O)_a(C_3H_6O)_b—]$ [Chem.27]

in which:

a is an integer greater than or equal to 1, preferably ranging from 5 to 200 and more particularly ranging from 10 to 100;

b is an integer of between 0 and 200, preferably ranging from 4 to 100 and more particularly between 5 and 30;

x is an integer ranging from 1 to 10 000 and more particularly from 10 to 5000;

R" is a hydrogen atom or a methyl;

R, which may be identical different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a radical $CH_2CH_2CH_2OCH_2CH(OH)CH_2$—; preferentially, R denotes a radical $CH_2CH_2CH_2OCH_2CH(OH)CH_2$—;

R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2$—; preferentially, R' denotes —$CH(CH_3)$—$CH_2$—.

The siloxane blocks preferably represent from 50 mol % to 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may in particular be made of the silicones sold under the name Silsoft A-843 or Silsoft A+ by Momentive.

g) and mixtures thereof.

Preferably, the amino silicones of formula (B) are chosen from the amino silicones corresponding to formula (E).

Preferably, the composition according to the invention comprises at least one amino silicone having the INCI name amodimethicone, preferably introduced in the form of an emulsion or microemulsion with surfactants.

Preferably, the composition according to the invention comprises at least one amino silicone having the INCI name amodimethicone as an emulsion or microemulsion with surfactants, having the INCI names trideceth-5 and trideceth-10.

The silicone(s) may be present in a total amount ranging from 0.01% to 20% by weight relative to the total weight of the composition, preferably from 0.05% to 15% by weight, more preferentially from 0.1% to 10% by weight, more preferentially from 0.1% to 5% by weight relative to the total weight of composition (C).

When composition (C) comprises one or more amino silicones, the total amount of amino silicone(s) may range from 0.01% to 20% by weight, preferably from 0.05% to 15% by weight, better still from 0.1% to 10% by weight and more preferentially from 0.1% to 5% by weight relative to the total weight of composition (C).

Coloring Agent:

Composition (C) according to the invention comprises at least one coloring agent chosen from pigments, direct dyes and mixtures thereof.

Preferably, composition (C) according to the invention comprises one or more pigments.

The term "pigment" means any pigment that gives color to keratin materials. Their solubility in water at 25° C. and at atmospheric pressure (760 mmHg) is less than 0.05% by weight, and preferably less than 0.01%.

The pigments that may be used are notably chosen from the organic and/or mineral pigments known in the art, notably those described in Kirk-Othmer's Encyclopedia of Chemical Technology and in Ullmann's Encyclopedia of Industrial Chemistry.

They may be natural, of natural origin, or non-natural.

These pigments may be in pigment powder or paste form. They may be coated or uncoated.

The pigments may be chosen, for example, from mineral pigments, organic pigments, lacquers, pigments with special effects such as nacres or glitter flakes, and mixtures thereof.

The pigment may be a mineral pigment. The term "mineral pigment" refers to any pigment that satisfies the definition in Ullmann's encyclopedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" refers to any pigment that satisfies the definition in Ullmann's encyclopedia in the chapter on organic pigments.

The organic pigment may notably be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

In particular, the white or colored organic pigments may be chosen from carmine, carbon black, aniline black, azo yellow, quinacridone, phthalocyanine blue, the blue pigments codified in the Color Index under the references CI 42090, 69800, 69825, 74100, 74160, the yellow pigments codified in the Color Index under the references CI 11680, 11710, 19140, 20040, 21100, 21108, 47000, 47005, the green pigments codified in the Color Index under the references CI 61565, 61570, 74260, the orange pigments codified in the Color Index under the references CI 11725, 45370, 71105, the red pigments codified in the Color Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives as described in patent FR 2 679 771.

Examples that may also be mentioned include pigment pastes of organic pigments, such as the products sold by the company Hoechst under the names:

Cosmenyl Yellow IOG: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Cosmenyl Carmine FB: Red 5 pigment (CI 12490);
Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1 184 426. These composite pigments may be composed notably of particles including a mineral core, at least one binder, for attaching the organic pigments to the core, and at least one organic pigment which at least partially covers the core.

The organic pigment may also be a lake. The term "lake" refers to dyes adsorbed onto insoluble particles, the assembly thus obtained remaining insoluble during use.

The inorganic substrates onto which the dyes are adsorbed are, for example, alumina, silica, calcium sodium borosilicate, calcium aluminum borosilicate and aluminum.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a colored appearance (characterized by a certain shade, a certain vivacity and a certain level of luminance) that is non-uniform and that changes as a function of the conditions of observation (light, temperature, angles of observation, etc.). They thereby differ from colored pigments, which afford a standard uniform opaque, semi-transparent or transparent shade.

Several types of pigments with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, colored nacreous pigments such as titanium mica with iron oxides, mica covered with iron oxide, titanium mica notably with ferric blue or with chromium oxide, titanium mica with an organic pigment of the abovementioned type, and also nacreous pigments based on bismuth oxychloride. Nacreous pigments that may be mentioned include the Cellini nacres sold by BASF (mica-TiO2-lake), Prestige sold by Eckart (mica-TiO2), Prestige Bronze sold by Eckart (mica-Fe2O3), and Colorona sold by Merck (mica-TiO2-Fe2O3).

Mention may also be made of the gold-colored nacres sold notably by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold notably by the company Merck under the name Bronze fine (17384) (Colorona) and Bronze (17353) (Colorona) and by the company BASF under the name Super bronze (Cloisonne); the orange nacres sold notably by the company BASF under the name Orange 363C(Cloisonne) and Orange MCR 101 (Cosmica) and by the company Merck under the name Passion orange (Colorona) and Matte orange (17449) (Microna); the brown nacres sold notably by the company BASF under the name Nu-antique copper 340XB (Cloisonne) and Brown CL4509 (Chromalite); the nacres with a copper tint sold notably by the company BASF under the name Copper 340A (Timica); the nacres with a red tint sold notably by the company Merck under the name Sienna fine (17386) (Colorona); the nacres with a yellow tint sold notably by the company BASF under the name Yellow (4502) (Chromalite); the red nacres with a gold tint sold notably by the company BASF under the name Sunstone G012 (Gemtone); the pink nacres sold notably by the company BASF under the name Tan opale G005 (Gemtone); the black nacres with a gold tint sold notably by the company BASF under the name Nu antique bronze 240 AB (Timica), the blue nacres sold notably by the company Merck under the name Matte blue (17433) (Microna), the white nacres with a silvery tint sold notably by the company Merck under the name Xirona Silver, and the golden-green pink-orange nacres sold notably by the company Merck under the name Indian summer (Xirona), and mixtures thereof.

Still as examples of nacres, mention may also be made of particles including a borosilicate substrate coated with titanium oxide.

Particles comprising a glass substrate coated with titanium oxide are notably sold under the name Metashine MC1080RY by the company Toyal.

Finally, examples of nacres that may also be mentioned include polyethylene terephthalate flakes, notably those sold by the company Meadowbrook Inventions under the name Silver 1P 0.004X0.004 (silver flakes). Multilayer pigments based on synthetic substrates such as alumina, silica, sodium calcium borosilicate or calcium aluminum borosilicate, and aluminum, may also be envisaged.

The pigments with special effects may also be chosen from reflective particles, i.e. notably from particles whose size, structure, notably the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment by appearing to sparkle.

The reflective particles may be selected so as not to significantly alter the coloring effect generated by the coloring agents with which they are combined, and more particularly so as to optimize this effect in terms of color rendition. They may more particularly have a yellow, pink, red, bronze, orange, brown, gold and/or coppery color or tint.

These particles may have varied forms and may notably be in platelet or globular form, in particular in spherical form.

Irrespective of their form, the reflective particles may or may not have a multilayer structure, and, in the case of a multilayer structure, may have, for example, at least one layer of uniform thickness, notably of a reflective material.

When the reflective particles do not have a multilayer structure, they may be composed, for example, of metal oxides, notably titanium or iron oxides obtained synthetically.

When the reflective particles have a multilayer structure, they may include, for example, a natural or synthetic substrate, notably a synthetic substrate at least partially coated with at least one layer of a reflective material, notably of at least one metal or metallic material. The substrate may be made of one or more organic and/or mineral materials.

More particularly, it may be chosen from glasses, ceramics, graphite, metal oxides, aluminas, silicas, silicates, notably aluminosilicates and borosilicates, and synthetic mica, and mixtures thereof, this list not being limiting.

The reflective material may include a layer of metal or of a metallic material.

Reflective particles are notably described in JP-A-09188830, JP-A-10158450, JP-A-10158541, JP-A-07258460 and JP-A-05017710.

Still as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the names Crystal Star GF 550 and GF 2525 by this same company.

Use may also be made of particles comprising a metallic substrate such as silver, aluminum, iron, chromium, nickel, molybdenum, gold, copper, zinc, tin, manganese, steel, bronze or titanium, said substrate being coated with at least one layer of at least one metal oxide such as titanium oxide, aluminum oxide, iron oxide, cerium oxide, chromium oxide or silicon oxides, and mixtures thereof.

Examples that may be mentioned include aluminum powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colors, and also particular optical effects such as metallic effects or interference effects.

The size of the pigment used in the composition according to the present invention is generally between 10 nm and 200

μm, preferably between 20 nm and 80 μm and more preferentially between 30 nm and 50 μm.

The pigments may be dispersed in the composition by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters and $C_8$ to $C_{20}$ fatty acid esters of polyols such as glycerol or diglycerol are used, such as poly(12-hydroxystearic acid) stearate with a molecular weight of approximately 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225C.

The pigments used in the composition may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described notably in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminum salts of fatty acids, for example aluminum stearate or laurate; metal alkoxides; polyethylene; (meth)acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; fluorosilicone compounds.

The surface-treated pigments that are useful in the composition may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in U.S. Pat. No. 4,578,266.

An organic agent covalently bonded to the pigments will preferably be used.

The agent for the surface treatment may represent from 0.1% to 50% by weight relative to the total weight of the surface-treated pigment, preferably from 0.5% to 30% by weight and even more preferentially from 1% to 20% by weight relative to the total weight of the surface-treated pigment.

Preferably, the surface treatments of the pigments are chosen from the following treatments:

- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a magnesium myristate treatment, for instance the MM surface treatment sold by LCW;
- an aluminum dimyristate treatment, such as the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrosiloxane/perfluoroalkyl phosphate treatment, for instance the FS01 surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- an acrylate copolymer treatment, for instance the APD surface treatment sold by Daito;
- a perfluoroalkyl phosphate/isopropyl titanium triisostearate treatment, for instance the PF+ITT surface treatment sold by Daito.

According to a particular embodiment of the invention, the dispersant is present with organic or mineral pigments in submicron-sized particulate form in the dye composition.

The term “submicron” or “submicronic” refers to pigments having a particle size that has been micronized by a micronization method and having a mean particle size of less than a micrometer (μm), in particular between 0.1 and 0.9 μm, and preferably between 0.2 and 0.6 μm.

According to one embodiment, the dispersant and the pigment(s) are present in an amount (dispersant:pigment) of between 1:4 and 4:1, particularly between 1.5:3.5 and 3.5:1 or better still between 1.75:3 and 3:1.

The dispersant(s) may therefore have a silicone backbone, such as silicone polyether and dispersants of aminosilicone type other than the silicones described previously. Among the suitable dispersants, mention may be made of:

aminosilicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers, silicone acrylates such as Tego® RC 902, Tego® RC 922, Tego® RC 1041, and Tego® RC 1043, sold by Evonik, polydimethylsiloxane (PDMS) silicones with carboxyl groups such as X-22162 and X-22370 by Shin-Etsu, epoxy silicones such as GP-29, GP-32, GP-502, GP-504, GP-514, GP-607, GP-682, and GP-695 by Genesee Polymers, or Tego® RC 1401, Tego® RC 1403, Tego® RC 1412 by Evonik.

According to a particular embodiment, the dispersant(s) are of amino silicone type other than the silicones described previously and are cationic.

Preferably, the pigment(s) are chosen from mineral, mixed mineral-organic or organic pigments.

In one variant of the invention, the pigment(s) according to the invention are organic pigments, preferentially organic pigments surface-treated with an organic agent chosen from silicone compounds. In another variant of the invention, the pigment(s) according to the invention are mineral pigments.

Composition (C) may comprise one or more direct dyes.

The term "direct dye" means natural and/or synthetic dyes, other than oxidation dyes. These are dyes that will spread superficially on the fiber.

They may be ionic or nonionic, preferably cationic or nonionic.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (XII) and (XIII) and the azo cationic dyes (XIV) and (XV) below:

[Chem.29]

$$Hét^{+}\text{-}C(Ra){=}N{-}N(Rb){-}Ar,Q \quad (XIII)$$

[Chem.30]

$$Hét^{+}\text{-}N(Ra){-}N{=}C(Rb){-}Ar,Q- \quad (XIII)$$

[Chem.31]

$$Hét^{+}\text{-}N{=}N{-}Ar,Q- \quad (XIV)$$

[Chem.32]

$$Ar^{+}{-}N{=}N{-}Ar'',Q- \quad (XV)$$

in which formulae (XII) to (XV):

Het+ represents a cationic heteroaryl radical, preferentially bearing an endocyclic cationic charge, such as imidazolium, indolium or pyridinium, which is optionally substituted, preferentially with at least one ($C_1$-$C_8$) alkyl group such as methyl;

$Ar^+$ represents an aryl radical, such as phenyl or naphthyl, bearing an exocyclic cationic charge, preferentially ammonium, particularly tri($C_1$-$C_8$)alkylammonium, such as trimethylammonium;

Ar represents an aryl group, notably phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar" represents an optionally substituted (hetero)aryl group, such as phenyl or pyrazolyl, which are optionally substituted, preferentially with one or more ($C_1$-$C_8$)alkyl, hydroxyl, (di)($C_1$-$C_8$)(alkyl)amino, ($C_1$-$C_8$) alkoxy or phenyl groups;

Ra and Rb, which may be identical or different, represent a hydrogen atom or a ($C_1$-$C_8$)alkyl group, which is optionally substituted, preferentially with a hydroxyl group;

or else the substituent Ra with a substituent of $Het^+$ and/or Rb with a substituent of Ar form, together with the atoms that bear them, a (hetero)cycloalkyl; in particular, Ra and Rb represent a hydrogen atom or a ($C_1$-$C_4$)alkyl group optionally substituted with a hydroxyl group;

Q- represents an organic or mineral anionic counterion, such as a halide or an alkyl sulfate.

In particular, mention may be made of the azo and hydrazono direct dyes bearing an endocyclic cationic charge of formulae (XII) to (XV) as defined previously, more particularly, the cationic direct dyes bearing an endocyclic cationic charge described in patent applications WO 95/15144, WO 95/01772 and EP 714 954, preferentially the following direct dyes:

[Chem. 33]

(XVI)

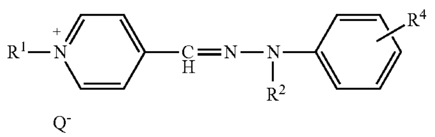

[Chem. 34]

(XVII)

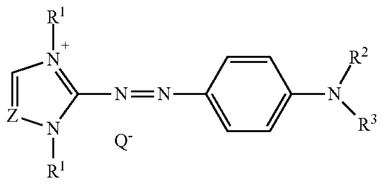

in which formulae (XVI) and (XVII):

$R^1$ represents a ($C_1$-$C_4$)alkyl group such as methyl;

$R^2$ and $R^3$, which may be identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group (s) with a hydroxyl group; particularly, $R^4$ is a hydrogen atom, Z represents a CH group or a nitrogen atom, preferentially CH, Q- is an anionic counterion as defined previously, in particular a halide, such as chloride, or an alkyl sulfate, such as methyl sulfate or mesityl;

In particular, the dyes of formulae (XVII) and (XVIII) are chosen from Basic Red 51, Basic Yellow 87 and Basic Orange 31 or derivatives thereof with Q' being an anionic counterion as defined previously, particularly halide such as chloride, or an alkyl sulfate such as methyl sulfate or mesityl.

The direct dyes may be chosen from anionic direct dyes. The anionic direct dyes of the invention are dyes commonly referred to as "acid" direct dyes owing to their affinity for alkaline substances. The term "anionic direct dye" means any direct dye including in its structure at least one $CO_2R$ or $SO_3R$ substituent with R denoting a hydrogen atom or a cation originating from a metal or an amine, or an ammonium ion. The anionic dyes may be chosen from direct nitro acid dyes, azo acid dyes, azine acid dyes, triarylmethane acid dyes, indoamine acid dyes, anthraquinone acid dyes, indigoid dyes and natural acid dyes.

As acid dyes according to the invention, mention may be made of the dyes of formulae (XVIII), (XVIII'), (XIX), (XIX'), (XX), (XX'), (XXI), (XXI'), (XXII), (XXIII), (XXIV) and (XXV) below:

a) the diaryl anionic azo dyes of formula (XVIII) or (XVIII'):

[Chem. 35]

(XVIII)

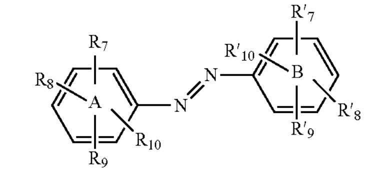

[Chem. 36]

(XVIII')

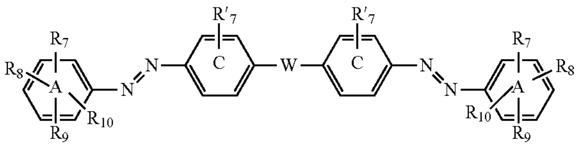

in which formulae (XVIII) and (XVIII'):

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;

nitro, nitroso;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

$(O)_2S(O—)$—, M+ with M+ representing a hydrogen atom or a cationic counterion;

$(O)CO^-$—, $M^+$ with $M^+$ as defined previously;

R"—$S(O)_2$—, with R" representing a hydrogen atom or an alkyl, aryl, (di)(alkyl)amino or aryl(alkyl)amino group; preferentially a phenylamino or phenyl group;

R'"—$S(O)_2$—X'— with R'" representing an alkyl or optionally substituted aryl group, X' as defined previously;

(di)(alkyl)amino;

aryl(alkyl)amino optionally substituted with one or more groups chosen from i) nitro; ii) nitroso; iii) (O)2S (O—)—, M+ and iv) alkoxy with M+ as defined previously;

optionally substituted heteroaryl; preferentially a benzothiazolyl group;

cycloalkyl; notably cyclohexyl;

Ar—N═N— with Ar representing an optionally substituted aryl group, preferentially a phenyl optionally substituted with one or more alkyl, (O)2S(O—)—, M+ or phenylamino groups;

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O—)$—, M+; iv) hydroxyl; v) mercapto; vi) (di)(alkyl)amino; vii) R°—C(X)—X'—; viii) R°—X'—C(X)—; ix) R°—X'—C(X)—X"—; x) Ar—N═N— and xi) optionally substituted aryl(alkyl)amino; with M+, R°, X, X', X" and Ar as defined previously;

W represents a sigma bond a, an oxygen or sulfur atom, or a divalent radical i) —NR— with R as defined previously, or ii) methylene —C(Ra)(Rb)— with Ra and Rb, which may be identical or different, representing a hydrogen atom or an aryl group, or alternatively Ra and Rb form, with the carbon atom that bears them, a spiro cycloalkyl; preferentially, W represents a sulfur atom or Ra and Rb together form a cyclohexyl; it being understood that formulae (XVIII) and (XVIII') comprise at least one sulfonate radical $(O)_2S(O—)$—, M+ or one carboxylate radical (O)CO—, M+ on one of the rings A, A', B, B' or C; preferentially sodium sulfonate.

As examples of dyes of formula (XVIII), mention may be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment Red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food yellow 3 or sunset yellow;

and, as examples of dyes of formula (XVIII'), mention may be made of: Acid Red 111, Acid Red 134, Acid yellow 38.

b) the pyrazolone anionic azo dyes of formulae (XIX) and (XIX'):

[Chem. 37]

(XIX)

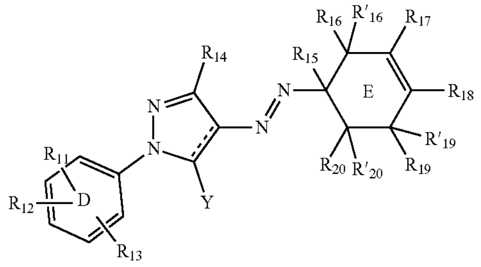

[Chem. 38]

(XIX')

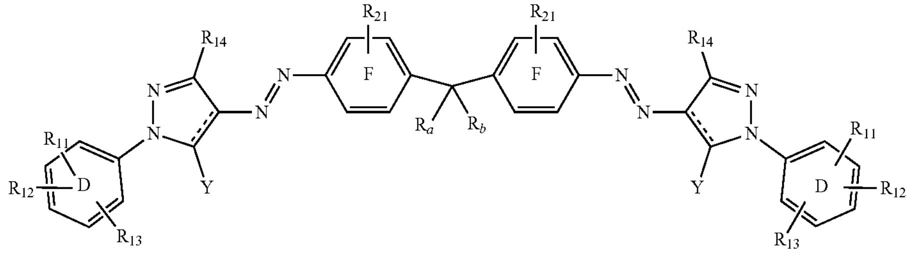

in which formulae (XIX) and (XIX'):

$R_{11}$, $R_{12}$ and $R_{13}$, which may be identical or different, represent a hydrogen or halogen atom, an alkyl group or —$(O)_2S(O$—), M+ with M+ as defined previously;

$R_{14}$ represents a hydrogen atom, an alkyl group or a group —C(O)O—, M+ with M+ as defined previously;

$R_{15}$ represents a hydrogen atom;

$R_{16}$ represents an oxo group, in which case $R'_{16}$ is absent, or alternatively $R_{15}$ with $R_{16}$ together form a double bond;

$R_{17}$ and $R_{18}$, which may be identical or different, represent a hydrogen atom, or a group chosen from:

$(O)_2S(O$—)—, M+ with M+ as defined previously;

Ar—O—$S(O)_2$— with Ar representing an optionally substituted aryl group; preferentially a phenyl optionally substituted with one or more alkyl groups;

$R_{19}$ and $R_{20}$ together form either a double bond, or a benzo group D', which is optionally substituted;

$R'_{16}$, $R'_{19}$ and $R'_{20}$, which may be identical or different, represent a hydrogen atom or an alkyl or hydroxyl group;

$R_{21}$ represents a hydrogen atom or an alkyl or alkoxy group;

$R_a$ and $R_b$, which may be identical or different, are as defined previously, preferentially $R_a$ represents a hydrogen atom and $R_b$ represents an aryl group;

Y represents either a hydroxyl group or an oxo group;

- - - - represents a single bond when Y is an oxo group; and represents a double bond when Y represents a hydroxyl group;

it being understood that formulae (XIX) and (XIX') comprise at least one sulfonate radical $(O)_2S(O$—)—, M+ or one carboxylate radical —C(O)O—, M+ on one of the rings D or E; preferentially sodium sulfonate.

As examples of dyes of formula (XIX), mention may be made of: Acid Red 195, Acid Yellow 23, Acid Yellow 27, Acid Yellow 76, and as examples of dyes of formula (XX'), mention may be made of: Acid Yellow 17;

c) the anthraquinone dyes of formulae (XX) and (XX'):

[Chem. 39]

(XX)

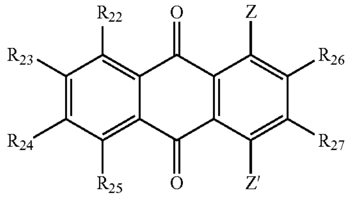

[Chem. 40]

(XX')

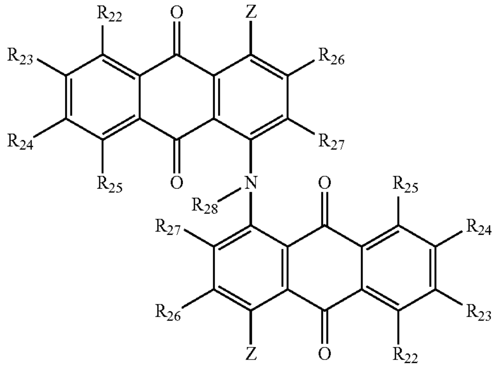

in which formulae (XX) and (XX'):

$R_{22}$, $R_{23}$, $R_{24}$, $R_{25}$, $R_{26}$ and $R_{27}$, which may be identical or different, represent a hydrogen or halogen atom, or a group chosen from:

alkyl;

hydroxyl, mercapto;

alkoxy, alkylthio;

optionally substituted aryloxy or arylthio, preferentially substituted with one or more groups chosen from alkyl and $(O)_2S(O—)—$, M+ with M+ as defined previously;

aryl(alkyl)amino optionally substituted with one or more groups chosen from alkyl and (O)2S(O—)—, M+ with M+ as defined previously;

(di)(alkyl)amino;

(di)(hydroxyalkyl)amino;

$(O)_2S(O—)—$, M+ with M+ as defined previously;

Z' represents a hydrogen atom or a group NR28R29 with R28 and R29, which may be identical or different, representing a hydrogen atom or a group chosen from:

alkyl;

polyhydroxyalkyl such as hydroxyethyl;

aryl optionally substituted with one or more groups, particularly i) alkyl such as methyl, n-dodecyl, n-butyl; ii) $(O)_2S(O—)—$, M+ with M+ as defined previously; iii) R°—C(X)—X'—, R°—X'—C(X)—, R°—X'—C(X)—X"— with R°, X, X' and X" as defined previously, preferentially R° represents an alkyl group;

cycloalkyl; notably cyclohexyl;

Z, represents a group chosen from hydroxyl and NR'28R'29 with R'28 and R'29, which may be identical or different, representing the same atoms or groups as R28 and R29 as defined previously; it being understood that formulae (XXI) and (XXI') comprise at least one sulfonate radical $(O)_2S(O—)—$, M+ or one carboxylate radical C(O)O—, M+; preferentially sodium sulfonate.

As examples of dyes of formula (XXI), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT violet No. 2; and, as an example of a dye of formula (XXI'), mention may be made of: Acid Black 48;

d) the nitro dyes of formulae (XXI) and (XXI'):

[Chem. 41]

(XXI)

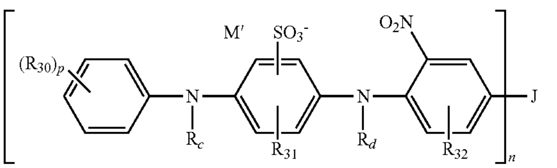

[Chem. 42]

(XXI')

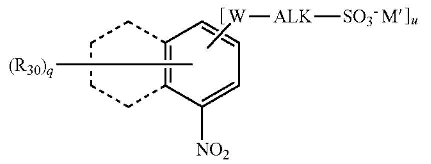

in which formulae (XXI) and (XXI'):

$R_{30}$, $R_{31}$ and $R_{32}$, which may be identical or different, represent a hydrogen or halogen atom, or a group chosen from:

alkyl;

alkoxy optionally substituted with one or more hydroxyl groups, alkylthio optionally substituted with one or more hydroxyl groups;

hydroxyl, mercapto;

nitro, nitroso;

polyhaloalkyl;

R°—C(X)—X'—, R°—X'—C(X)—, R°—X'—C(X)—X"— with R°, X, X' and X" as defined previously;

$(O)_2S(O—)—$, M+ with M+ as defined previously;

$(O)CO^-—$, $M^+$ with $M^+$ as defined previously;

(di)(alkyl)amino;

(di)(hydroxyalkyl)amino;

heterocycloalkyl such as piperidino, piperazino or morpholino; in particular, $R_{30}$, $R_{31}$ and $R_{32}$ represent a hydrogen atom;

Rc and Rd, which may be identical or different, represent a hydrogen atom or an alkyl group;

W is as defined previously; W particularly represents an —NH— group;

ALK represents a linear or branched divalent $C_1$-$C_6$ alkylene group; in particular, ALK represents a $—CH_2—CH_2—$ group;

n is 1 or 2;

p represents an integer inclusively between 1 and 5;

q represents an integer inclusively between 1 and 4;

u is 0 or 1;

when n is 1, J represents a nitro or nitroso group; particularly nitro;

when n is 2, J represents an oxygen or sulfur atom, or a divalent radical —S(O)m- with m representing an integer 1 or 2; preferentially, J represents an —SO2- radical;

M' represents a hydrogen atom or a cationic counterion;

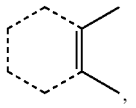

which may be present or absent, represents a benzo group optionally substituted with one or more groups R30 as defined previously;

it being understood that formulae (XXI) and (XXI') comprise at least one sulfonate radical $(O)_2S(O—)$-, M+ or one carboxylate radical —C(O)O—, M+; preferentially sodium sulfonate.

As examples of dyes of formula (XXII), mention may be made of: Acid Brown 13 and Acid Orange 3; as examples of dyes of formula (XXII'), mention may be made of: Acid Yellow 1, the sodium salt of 2,4-dinitro-1-naphthol-7-sulfonic acid, 2-piperidino-5-nitrobenzenesulfonic acid, 2-(4'-N, N-(2"-hydroxyethyl)amino-2'-nitro)anilineethanesulfonic acid, 4-β-hydroxyethylamino-3-nitrobenzenesulfonic acid; EXT D&C Yellow 7;

e) the triarylmethane dyes of formula (XXII):

[Chem. 43]

(XXII)

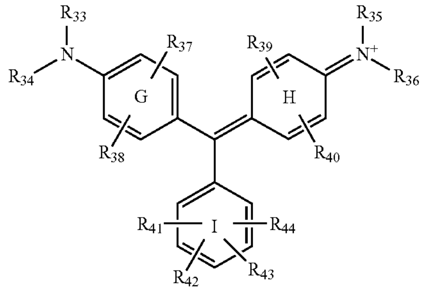

in which formula (XXII):

$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl and benzyl group optionally substituted with a group $(O)_mS(O—)—$, M+ with M+ and m as defined previously;

$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:

alkyl;

alkoxy, alkylthio;

(di)(alkyl)amino;

hydroxyl, mercapto;

nitro, nitroso;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

$(O)_2S(O—)—$, M+ with M+ representing a hydrogen atom or a cationic counterion;

$(O)CO^-—$, $M^+$ with $M^+$ as defined previously;

or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O—)—$, M+; iv) hydroxyl; v) mercapto; vi) (di)(alkyl)amino; vii) R°—C(X)—X'—; viii) R°—X'—C(X)— and ix) R°—X'—C(X)—X"—; with M+, R°, X, X' and X" as defined previously;

in particular, $R_{37}$ to $R_{40}$ represent a hydrogen atom, and $R_{41}$ to $R_{44}$, which may be identical or different, represent a hydroxyl group or $(O)_2S(O—)—$, M+; and when $R_{43}$ with $R_{44}$ together form a benzo group, it is preferentially substituted with an $(O)_2S(O—)—$ group;

it being understood that at least one of the rings G, H, I or I' comprises at least one sulfonate radical $(O)_2S(O—)—$ or a carboxylate radical —C(O)O—; preferentially sulfonate;

As examples of dyes of formula (XXIII), mention may be made of: Acid Blue 1; Acid Blue 3; Acid Blue 7, Acid Blue 9; Acid Violet 49; Acid Green 3; Acid Green 5 and Acid Green 50;

f) the xanthene-based dyes of formula (XXIII):

[Chem. 44]

(XXIII)

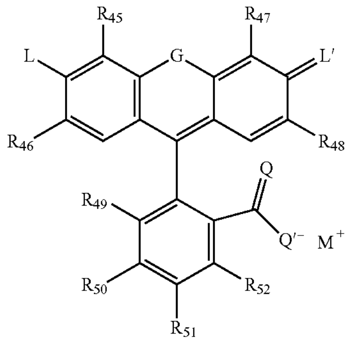

in which formula (XXIII):

$R_{45}$, $R_{46}$, $R_{47}$ and $R_{48}$, which may be identical or different, represent a hydrogen or halogen atom;

$R_{49}$, $R_{50}$, $R_{51}$ and $R_{52}$, which may be identical or different, represent a hydrogen or halogen atom, or a group chosen from:

alkyl;

alkoxy, alkylthio;

hydroxyl, mercapto;

nitro, nitroso;

$(O)_2S(O—)—$, M+ with M+ representing a hydrogen atom or a cationic counterion;

$(O)CO^-—$, $M^+$ with $M^+$ as defined previously;

particularly, $R_{53}$, $R_{54}$, $R_{55}$ and $R_{48}$ represent a hydrogen or halogen atom;

G represents an oxygen or sulfur atom or a group NRe with Re as defined previously; particularly G represents an oxygen atom;

L represents an alkoxide O—, M+; a thioalkoxide S—, M+ or a group NRf, with Rf representing a hydrogen atom or an alkyl group, and M+ as defined previously; M+ is particularly sodium or potassium;

L' represents an oxygen or sulfur atom or an ammonium group: N+RfRg, with Rf and Rg, which may be identical or different, representing a hydrogen atom or an optionally substituted alkyl or aryl group; L' particularly represents an oxygen atom or a phenylamino group optionally substituted with one or more alkyl or $(O)_mS(O—)—$, M+ groups with m and M+ as defined previously;

Q and Q', which may be identical or different, represent an oxygen or sulfur atom; in particular, Q and Q' represent an oxygen atom;

M+ is as defined previously.

As an example of dyes of formula (XXIII), mention may be made of: Acid Yellow 73; Acid Red 51; Acid Red 52; Acid Red 87; Acid Red 92; Acid Red 95; Acid Violet 9;

g) the indole-based dyes of formula (XXIV):

[Chem. 45]

(XXIV)

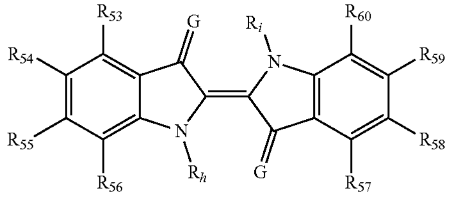

$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:

alkyl;

alkoxy, alkylthio;

hydroxyl, mercapto;

nitro, nitroso;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

$(O)_2S(O—)—$, M+ with M+ representing a hydrogen atom or a cationic counterion;

$(O)CO^-—$, $M^+$ with $M^+$ as defined previously;

G represents an oxygen or sulfur atom or a group NRe with Re as defined previously; particularly G represents an oxygen atom;

Ri and Rh, which may be identical or different, represent a hydrogen atom or an alkyl group; it being understood that formula (XXIV) comprises at least one sulfonate radical $(O)_2S(O—)—$, M+ or one carboxylate radical —C(O)O—, M+; preferentially sodium sulfonate.

As an example of dyes of formula (XXIV), mention may be made of: Acid Blue 74.

h) the quinoline-based dyes of formula (XXV):

[Chem. 46]

(XXV)

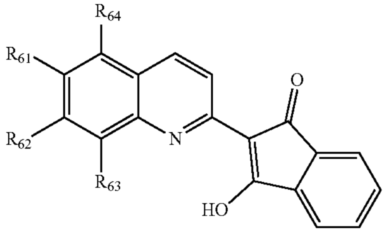

$R_{61}$ represents a hydrogen or halogen atom or an alkyl group;

$R_{62}$, $R_{63}$ and $R_{64}$, which may be identical or different, represent a hydrogen atom or a group $(O)_2S(O—)—$, M+ with M+ representing a hydrogen atom or a cationic counterion;

or alternatively $R_{61}$ with $R_{62}$, or $R_{61}$ with $R_{64}$, together form a benzo group optionally substituted with one or more groups $(O)_2S(O—)—$, M+ with M+ representing a hydrogen atom or a cationic counterion;

it being understood that formula (XXV) comprises at least one sulfonate radical $(O)_2S(O—)—$, M+ preferentially sodium sulfonate.

As examples of dyes of formula (XXVI), mention may be made of: Acid Yellow 2, Acid Yellow 3 and Acid Yellow 5.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

Preferably, the direct dye(s) are chosen from anionic direct dyes.

The coloring agent(s) may be present in a total content ranging from 0.001% to 20% by weight and preferably from 0.005% to 15% by weight relative to the total weight of composition (C).

The pigment(s) may be present in a total content ranging from 0.05% to 20% by weight, preferably from 0.1% to 15% by weight and better still from 1% to 10% by weight, relative to the total weight of composition (C).

The direct dye(s) may be present in a total content ranging from 0.001% to 10% by weight relative to the total weight of the composition, preferably from 0.005% to 5% by weight relative to the total weight of composition (C).

Composition (C) according to the invention may comprise water. Preferably, water is present in a content ranging from 0.1% to 95% by weight, more preferentially from 1% to 92% by weight and better still from 10% to 90% by weight relative to the total weight of the composition.

Organic Solvents:

Composition (C) according to the invention may comprise one or more organic solvents.

Examples of organic solvents that may be mentioned include lower $C_1$-$C_4$ alkanols, such as ethanol and isopropanol; polyols and polyol ethers, for instance glycerol, 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

The organic solvent(s) may be present in a total amount inclusively between 0.1% and 20% by weight approximately relative to the total weight of the dye composition, preferably between 0.5% and 15% by weight and more preferentially inclusively between 1% and 15% by weight relative to the total weight of composition (C).

Additives:

Composition (C) may also contain any adjuvant or additive usually used.

Among the additives that may be contained in the composition, mention may be made of reducing agents, thickeners, softeners, antifoams, moisturizers, UV-screening agents, peptizers, solubilizers, fragrances, anionic, cationic, nonionic or amphoteric surfactants, proteins, vitamins, polymers, preserving agents, waxes and mixtures thereof.

The composition according to the invention may notably be in the form of a suspension, a dispersion, a gel, an emulsion, notably an oil-in-water (O/W) or water-in-oil (W/O) emulsion, or a multiple emulsion (W/O/W or polyol/O/W or O/W/O), in the form of a cream, a mousse, a stick, a dispersion of vesicles, notably of ionic or nonionic lipids, or a two-phase or multi-phase lotion.

A person skilled in the art may select the appropriate presentation form, and also the method for preparing it, on the basis of his general knowledge, taking into account firstly the nature of the constituents used, notably their solubility in the support, and secondly the intended application of the composition.

Protocol:

The present invention also relates to a process for cosmetically treating, in particular dyeing, keratin fibers such as the hair, in which composition (C) as defined above is applied to said fibers.

Composition (C) described previously may be used on wet or dry keratin fibers, and also on any type of fair or dark, natural or dyed, permanent-waved, bleached or relaxed fibers.

According to a particular embodiment of the invention, the keratin fibers are washed before applying composition (C).

The application to the fibers may be performed via any standard means, in particular using a comb, a fine brush, a coarse brush, a sponge or with the fingers.

The application of composition (C) to the keratin fibers is generally performed at room temperature (between 15 and 25° C.).

Preferably, after applying composition (C) to the keratin fibers, one waits for between 1 minute and 6 hours, in particular between 1 minute and 2 hours, more particularly between 1 minute and 1 hour, more preferentially between 1 minute and 30 minutes, before, for example, a washing, rinsing, draining or drying step.

Preferably, a washing, rinsing, draining or drying step is implemented after applying composition (C) to the keratin fibers.

After applying composition (C), the fibers may be left to dry or may be dried, for example at a temperature of greater than or equal to 30° C.

The process according to the invention may thus comprise a step of applying heat to the keratin fibers using a heating tool.

The heat application step of the process of the invention may be performed using a hood, a hairdryer, a straightening iron, a curling iron, a Climazon, etc.

When the process of the invention involves a step of applying heat to the keratin fibers, the step of applying heat to the keratin fibers takes place after the application of composition (C) to the keratin fibers.

During the step of applying heat to the keratin fibers, a mechanical action may be exerted on the locks, such as combing, brushing or running the fingers through.

When the step of applying heat to the keratin fibers is performed using a hood or a hairdryer, the temperature is preferably between 30° C. and 110° C., preferentially between 50° C. and 90° C.

When the step of applying heat to the keratin fibers is performed using a straightening iron, the temperature is preferably between 110° C. and 220° C., preferably between 140° C. and 200° C.

In a particular variant, the process of the invention involves a step (b1) of applying heat using a hood, a hairdryer or a Climazon, preferably a hairdryer, and a step (b2) of applying heat using a straightening or curling iron, preferably a straightening iron.

Step (b1) may be performed before step (b2).

During step (b1), also referred to as the drying step, the fibers may be dried, for example at a temperature above or equal to 30° C. According to a particular embodiment, this temperature is above 40° C. According to a particular embodiment, this temperature is above 45° C. and below 110° C.

Preferably, if the fibers are dried, they are dried, in addition to a supply of heat, with a flow of air. This flow of air during drying makes it possible to improve the strand separation of the coating.

During drying, a mechanical action may be exerted on the locks, such as combing, brushing or running the fingers through.

During step (b2), the passage of the straightening or curling iron, preferably the straightening iron, may be performed at a temperature ranging from 110° C. to 220° C., preferably between 140° C. and 200° C.

After the drying step, a shaping step may be performed, for example with a straightening iron; the temperature for the shaping step is between 110 and 220° C., preferably between 140 and 200° C.

Preferably, the process according to the invention is a process for treating keratin fibers, such as the hair, comprising:

i) the application to said fibers of a composition (C) as defined previously, and then ii) optionally a leave-on time of said composition (C) on the fibers of from 1 minute to 30 minutes, preferably from 1 to 20 minutes, and then iii) optionally a step of washing, rinsing, draining or drying said fibers.

Preferably, the step of applying composition (C) to the keratin fibers is repeated several times.

According to another particular embodiment, the process for treating keratin fibers is a process for treating keratin fibers such as the hair, which consists in extemporaneously mixing, at the time of use, at least two compositions (C1) and (C2) and in applying the mixture to the keratin fibers, with:

- composition (C1) comprising at least one (poly)carbodiimide compound as described previously; and
- composition (C2) optionally comprising at least one aqueous dispersion of particles of polymer(s) chosen from polyurethanes, acrylic polymers, and mixtures thereof, as described previously;

composition (C1) and/or composition (C2) comprising at least one coloring agent chosen from pigments, direct dyes, and mixtures thereof, and optionally comprising at least one silicone as defined previously.

Preferably, composition (C2) comprises at least one coloring agent chosen from pigments, direct dyes, and mixtures thereof.

Preferably, composition (C1) does not comprise at least one coloring agent chosen from pigments, direct dyes, and mixtures thereof.

According to this embodiment, compositions (C1) and (C2) are mixed preferably less than 15 minutes before application to the keratin fibers, more preferentially less than 10 minutes before application, better still less than 5 minutes before application.

The weight ratio between composition (C1) and composition (C2) preferably ranges from 0.1 to 10, preferentially from 0.2 to 5 and better still from 0.5 to 2, or even from 0.6 to 1.5. In a particular embodiment, the weight ratio between composition (C1) and composition (C2) is equal to 1.

According to a particular variant of the invention, the present invention relates to a device for treating keratin fibers such as the hair, comprising at least two compartments containing:

- in a first compartment (F1), a composition (C1) comprising at least one (poly)carbodiimide compound as defined previously; and
- in a second compartment (F2), a composition (C2) optionally comprising at least one aqueous dispersion of particles of polymer(s) chosen from polyurethanes, acrylic polymers, and mixtures thereof, as defined previously;

composition (C1) and/or composition (C2) comprising at least one coloring agent chosen from pigments, direct dyes, and mixtures thereof, and optionally comprising at least one silicone as defined previously.

The present invention also relates to the use of composition (C) as defined previously for cosmetically treating, in particular dyeing, keratin fibers such as the hair.

The present invention will now be described more specifically by means of examples, which do not in any way limit the scope of the invention. However, the examples make it possible to support specific features, variants and preferred embodiments of the invention.

The (poly)carbodiimide(s) of the invention are accessible via synthetic methods known to those skilled in the art starting from commercial products or reagents that can be synthesized according to chemical reactions that are also known to those skilled in the art. Mention may be made, for example, of the book *Sciences of Synthesis*—Houben—Weyl Methods of Molecular Transformations, 2005, Georg Thiem Verlag Kg, Rudigerstrasse 14, D-70469 Stuttgart, or the U.S. Pat. No. 4,284,730 or the Canadian patent application CA 2 509 861.

More particularly, the process for preparing the (poly) carbodiimides of the invention involves, in a first step, a diisocyanate reagent (1):

$$O{=}C{=}N\text{-}L_1\text{-}N{=}C{=}O \quad (1)$$

Formula (1) wherein $L_1$ is as defined previously, which reacts in the presence of a carboimidation catalyst (2) such as those described in U.S. Pat. No. 4,284,730, notably phosphorus-based catalysts particularly chosen from phospholene oxides and phospholene sulfoxides, diaza- and oxaza-phospholanes, preferably under an inert atmosphere (nitrogen or argon), and in particular in a polar solvent which is preferably aprotic such as THF, glyme, diglyme, 1,4-dioxane or DMF, at a temperature between room temperature and the reflux temperature of the solvent, preferably at about 140° C.; to give the carbodiimide diisocyanate compound (3):

$$O{=}C{=}N\text{-}L_1\text{-}(N{=}C{=}N\text{-}L_1)_n\text{-}N{=}C{=}O \quad (3)$$

Formula (3) wherein $L_1$ and n are as defined previously. Benzoyl halogen such as benzoyl chloride may be added to deactivate the catalyst.

To obtain "symmetrical" (poly)carbodiimides, during the second step of the preparation process, compound (3) reacts with 1 molar equivalent (1 eq.) of nucleophilic reagent $R_1$—$X_1$—H and then 0.5 eq. of reagent H-E-H with $R_1$, $X_1$ and E as defined previously, to give the "symmetrical" compound according to the invention (4):

$$[R_1—X_1—C(O)—NH\text{-}L_1\text{-}(N{=}C{=}N\text{-}L_1)_n\text{-}NH—C(O)]_2\text{-}E \quad (4)$$

Formula (4) wherein $R_1$, $X_1$, $L_1$, n and E are as defined previously. According to one variant to obtain compound (4) from (3), it is possible first to add 0.5 eq. of reagent H-E-H and then 1 eq. of reagent $R_1$—$X_1$—H.

To obtain "dissymmetrical" (poly)carbodiimides, during the second step of the preparation process, compound (3) reacts with 1 molar equivalent (1 eq.) of nucleophilic reagent $R_1$—$X_1$—H and then 1 eq. of reagent H-E-H with $R_1$, $X_1$ and E as defined previously, to give compound (5):

$$R_1—X_1—C(O)—NH\text{-}L_1\text{-}(N{=}C{=}N\text{-}L_1)_n\text{-}NH—C(O)\text{-}E\text{-}H \quad (5)$$

Formula (5) wherein $R_1$, $X_1$, $L_1$, n and E are as defined previously.

According to one variant to obtain compound (5) from (3), it is possible first to add 1 eq. of reagent $R_1$—$X_1$—H and then 0.5 eq. of reagent H-E-H.

During a third step, compound (5) reacts with 1 eq. of compound (6):

$$R_2—X_2—C(O)—NH\text{-}L_1\text{-}(N{=}C{=}N\text{-}L_1)_z\text{-}N{=}C{=}O \quad (6),$$

said compound (6) is prepared beforehand from compound (3'):

$$O{=}C{=}N\text{-}L_1\text{-}(N{=}C{=}N\text{-}L_1)_z\text{-}N{=}C{=}O \quad (3'),$$

Formula (3') wherein $L_i$ and z are as defined previously, which reacts with 1 eq. of nucleophilic reagent $R_2$—$X_2$—H with $L_1$, $R_2$, $X_2$ and z as defined previously, to give the dissymmetrical compound (7):

$$R_1—X_1—C(O)—NH\text{-}L_1\text{-}(N{=}C{=}N\text{-}L_1)_n\text{-}NH—C(O)\text{-}E\text{-}C(O)—NH\text{-}L_1\text{-}(N{=}C{=}N\text{-}L_1)_z\text{-}NH—C(O)—X_2—R_2 \quad (7)$$

Formula (7) wherein $L_1$, $R_1$, $X_1$, $R_2$, $X_2$, n, z and E are as defined previously.

It is also possible to react 1 eq of compound (3') $O{=}C{=}N\text{-}L_1\text{-}(N{=}C{=}N\text{-}L_1)_z\text{-}N{=}C{=}O$ (3'), with 1/w equivalent of H-E-H then with 1 eq. of nucleophilic reagent $R_2$—$X_2$—H to give compound (8):

$$H\text{-}[E\text{-}C(O)—NH\text{-}L_1\text{-}(N{=}C{=}N\text{-}L_1)_z]_w\text{-}NH—C(O)—X_2\text{-}R_2 \quad (8)$$

Formula (8) wherein $L_1$, $R_2$, $X_2$, z and E are as defined previously, and w denotes an integer ranging from 1 to 3, preferably equal to 1.

The latter compound (8) can then react with 1 eq. of compound (4'):

$$R_1—X_1—C(O)—NH\text{-}L_1\text{-}(N{=}C{=}N\text{-}L_1)_n\text{-}N{=}C{=}O \quad (4')$$

(the said compound (4') can be synthetized by reaction of 0.5 eq. of nucleophilic reagent $R_1$—$X_1$—H with 1 eq. of compound (3)) to give the (poly)carbodiimide (9) of the invention:

$$R_1—X_1—C(O)—NH\text{-}L_1\text{-}(N{=}C{=}N\text{-}L_1)_n\text{-}NH—C(O)\text{-}[E\text{-}C(O)—NH\text{-}L_1\text{-}(N{=}C{=}N\text{-}L_1)_z]_w\text{-}NH—C(O)—X_2—R_2 \quad (9)$$

Formula (9) wherein $L_1$, $R_1$, $X_1$, $R_2$, $X_2$, n, z, w and E are as defined previously.

The (poly)carbodiimide compounds, and similarly all the reaction intermediates and reagents, may be purified via conventional methods known to those skilled in the art, such as extraction with water and water-immiscible organic solvent, facilitation, centrifugation, filtration and/or chromatography.

EXAMPLE

Example 1: Process for Synthesizing the (Poly)Carbodiimide Compound 50 g of 4,4'-dicyclohexylmethane diisocyanate and 0.5 g of 4,5-dihydro-3-methyl-1-phenyl-1H-phosphole 1-oxide were placed with stirring in a 500 mL three-necked round-bottomed flask equipped with a thermometer, a stirrer and a reflux tube.

The reaction medium was heated at 140° C. under nitrogen for 4 hours, the reaction being monitored by infrared spectroscopy by means of the absorption of the isocyanate functions between 2200 and 2300 $cm^{-1}$, and then cooled to 120° C.

A mixture of 5.3 g of polyethylene glycol monomer methyl ether and 1.2 g of 1,4-butanediol are introduced with stirring into the reaction medium. The temperature of 120° C. is maintained until the isocyanate functions have totally disappeared, monitored by infrared spectroscopy at 2200-2300 $cm^{-1}$, and is then cooled to room temperature.

After cooling to room temperature, the reaction medium is poured dropwise with vigorous stirring into a 500 mL glass beaker containing 85 g of distilled water, to give the desired product in the form of a translucent yellow liquid.

Example 2

Composition: amounts expressed in g of active material as obtained/100 g

TABLES 1

| Composition | C1 |
|---|---|
| Polycarbodiimide(1) | 24 |
| Amodimethicone (and) Trideceth-5 (and) Trideceth-10(2) | 5 |
| Preserving agent(s), optionally neutralized thickener | qs |
| Water | qs 100 |

(1)synthesized according to the synthetic process described in example 1 (containing 40% active material in water),
(2)sold by the company Wacker under the name Belsil ADM LOG 1

TABLES 2

| Composition | C2 |
|---|---|
| Acrylates copolymer(3) | 40 |
| Amodimethicone (and) Trideceth-5 (and) Trideceth-10(2) | 5 |
| Iron oxide (CI 77491) | 12 |
| Preserving agent(s), optionally neutralized thickener | qs |
| Water | qs 100 |

(3)sold by the company Daito Kasei Kogyo under the trade name Daitosol 3000SLPN-PE1 (aqueous dispersion containing 30% active material)

Composition C1 is mixed with composition C2 in a 50/50 ratio to obtain composition C.

Protocol:

Composition C is applied to locks of natural dry hair containing 90% white hairs, in a proportion of 0.5 g of composition per gram of lock.

The locks of hair are then dried with a hairdryer with a comb, and then combed.

The locks of hair are left at room temperature for 24 hours.

Next, the locks of hair thus dyed are then subjected to a test of several repeated shampoo washes so as to evaluate the fastness (persistence) of the coloring obtained with respect to shampoo washing.

Shampoo Wash Protocol:

The locks of dyed hair are combed and moistened with water at 35° C. before being passed between the fingers five times for 5 seconds. The locks of hair are then drained between two fingers.

A standard shampoo (Garnier Ultra Doux) is applied uniformly to the dyed locks, in a proportion of 0.4 g of standard shampoo per gram of locks, the locks of hair being massaged gently along the length (6 passes) for 15 seconds, from the root to the end.

The locks of hair are then placed in a watch glass and left to stand for 1 minute.

Next, the locks of hair are rinsed with water while passing the lock between the fingers (15 passes). The locks of hair are then drained between two fingers before the next shampoo wash.

Once the tests of several shampoo washes have been performed, the locks of hair are combed and dried with a hairdryer.

Results:

The persistence of the color of the locks was evaluated in the CIE L*a*b*system, using a Minolta Spectrophotometer CM3600A colorimeter (illuminant D65, angle 10°, specular component included).

In this L*a*b* system, L* represents the intensity of the color, a* indicates the green/red color axis and b* the blue/yellow color axis.

The persistence of the coloring is evaluated by the color difference ΔE between the dyed locks before shampooing, then after having undergone five shampoo washes according to the protocol described above. The lower the ΔE value, the more persistent the color with respect to shampoo washing.

The ΔE value is calculated according to the following equation:

$$\Delta E=\sqrt{(L^*-L_o^*)^2+(a^*-a_o^*)^2+(b^*-b_o^*)^2} \quad \text{[Math. 1]}$$

In this equation, L*a*b* represent the values measured after dyeing the hair and after performing the shampoo washes, and $L^*_0a_0{}^*b_0{}^*$ represent the values measured after dyeing the hair but before shampoo washing.

TABLES 3

| Compositions | Number of shampoo washes | L* | a* | b* | ΔE |
|---|---|---|---|---|---|
| Composition C | 0 | 36.0 | 29.0 | 22.3 | 0 |
| | 5 | 37.4 | 27.4 | 20.9 | 2.6 |

The locks of hair dyed with composition an washed with five shampoo washes show goo color persistence with respect to shampoo washing.

Example 3

Composition: amounts expressed in g of active material as obtained/100 g

TABLES 4

| Composition | C' |
|---|---|
| Polycarbodiimide(1) | 12 |
| Amodimethicone (and) Trideceth-5 (and) Trideceth-10(2) | 5 |
| Acrylates copolymer(3) | 20 |
| Iron oxide (CI 77491) | 6 |
| Preserving agent(s), optionally neutralized thickener | qs |
| Water | qs 100 |

(1)synthesized according to the synthetic process described in example 1 (containing 40% active material in water).
(2)sold by the company Wacker under the name Belsil ADM LOG 1
(3)sold by the company Daito Kasei Kogyo under the trade name Daitosol 3000SLPN-PE1 (aqueous dispersion containing 30% active material)

Protocol:

Composition C' is applied to locks of natural dry hair containing 90% white hairs, in a proportion of 0.5 g of composition per gram of lock.

The locks of hair are then dried with a hairdryer with a comb, and then combed.

The locks of hair are left at room temperature for 24 hours.

Results:

The locks of hair treated with composition C' show smooth, uniform, colored coating of the hair and have good cosmetic properties, notably in terms of softness, feel and good hair strand separation. The colored coating of the keratin fibers shows good persistence with respect to shampoo washing.

Example 4

Composition: amounts expressed in g of active material as obtained/100 g

TABLES 5

| Composition | A1 (invention) | B1 (comparative) |
|---|---|---|
| Polycarbodiimided(1) | 24 (9.6 AM) | — |
| Carbodilite E-05 sold by the company Nisshinbo Chemical Inc. (containing 41.3% active material in water) | — | 23.3 (9.6 AM) |
| Amodimethicone (and) Trideceth-5 (and) Trideceth-10(2) | 5 | 5 |
| Water | qs 100 | qs 100 |

(1)synthesized according to the synthetic process described in example 1 (containing 40% active material in water),
(2)sold by the company Wacker under the name Belsil ADM LOG 1

TABLES 6

| Composition | A2 |
|---|---|
| Acrylates copolymer(3) | 40 |
| Amodimethicone (and) Trideceth-5 (and) Trideceth-10(2) | 5 |
| Iron oxide (CI 77491) | 12 |
| Water | qs 100 |

(3)sold by the company Daito Kasei Kogyo under the trade name Daitosol 3000SLPN-PE1 (aqueous dispersion containing 30% active material)

Composition A1 is mixed with composition A2 in a 50/50 ratio to obtain composition A according to the invention.

Composition B1 is mixed with composition A2 in a 50/50 ratio to obtain comparative composition B.

Protocol:

Composition A and composition B are applied to locks of natural dry hair containing 90% white hairs, in a proportion of 0.5 g of composition per gram of lock.

The locks of hair are then dried with a hairdryer with a comb, and then combed.

The locks of hair are left at room temperature for 24 hours.

Next, the locks of hair thus dyed are then subjected to a test of several repeated shampoo washes so as to evaluate the fastness (persistence) of the coloring obtained with respect to shampoo washing.

Shampoo wash protocol is the same as the protocol described in example 2.

Results:

The persistence of the color of the locks was evaluated in the CIE L*a*b* system, using a Minolta Spectrophotometer CM3600A colorimeter (illuminant D65, angle 10°, specular component included).

In this L*a*b* system, L* represents the intensity of the color, a* indicates the green/red color axis and b* the blue/yellow color axis.

The persistence of the coloring is evaluated by the color difference ΔE between the dyed locks before shampooing, then after having undergone three shampoo washes according to the protocol described in example 2. The lower the ΔE value, the more persistent the color with respect to shampoo washing.

The ΔE value is calculated according to the following equation:

$$\Delta E=\sqrt{(L^*-L_0^*)^2+(a^*-a_0^*)^2+(b^*-b_0^*)^2} \quad \text{[Math. 1]}$$

In this equation, L*a*b* represent the values measured after dyeing the hair and after performing the shampoo washes, and $L^*_0a_0{}^*b_0{}^*$ represent the values measured after dyeing the hair but before shampoo washing.

TABLES 7

| Compositions | Number of shampoo washes | L* | a* | b* | ΔE |
|---|---|---|---|---|---|
| Composition A | 0 | 35.95 | 26.62 | 19.47 | — |
| (invention) | 3 | 41.51 | 21.87 | 17.07 | 7.70 |
| Composition B | 0 | 37.23 | 28.47 | 20.89 | — |
| (comparative) | 3 | 47.4 | 15.78 | 15.22 | 17.22 |

The locks of hair dyed with the composition A according to the invention and washed with three shampoo washes have ΔE values that are lower than those of the locks of hair dyed with the comparative composition B.

Thus, the colored coating of the keratin fibers obtained with the composition A according to the invention shows good persistence with respect to shampoo washing. Specifically, the locks of hair dyed with the composition A according to the invention and washed with three shampoo washes have better persistence of the color than the locks of hair dyed with the comparative composition B.

The invention claimed is:

1. A composition for dyeing hair, comprising:

a) at least one (poly) carbodiimide compound chosen from compounds of formula (I) below:

(I)

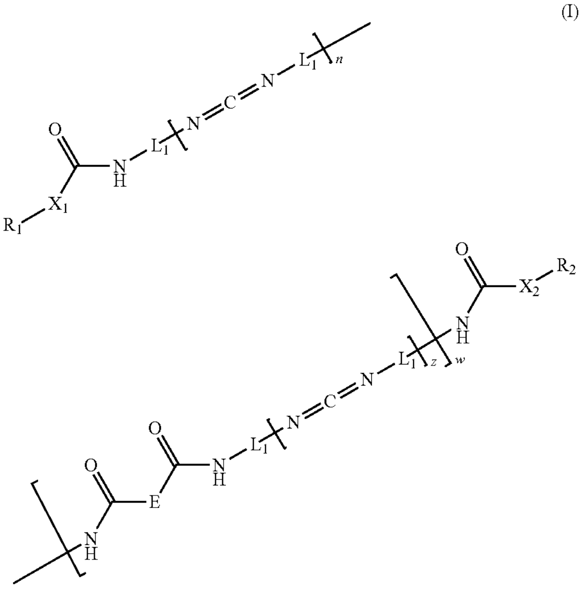

wherein:

$X_1$ and $X_2$ independently represent an oxygen atom, a sulfur atom, or an —NH group;

$R_1$ and $R_2$ independently represent a hydrocarbon-based radical, optionally interrupted with one or more heteroatoms;

n and z independently denote an integer ranging from 1 to 20;

w denotes an integer ranging from 1 to 3;

$L_1$ independently represents a $C_1$-$C_{18}$ divalent aliphatic hydrocarbon-based radical, a $C_3$-$C_{15}$ cycloalkylene radical, a $C_3$-$C_{12}$ heterocycloalkylene group, or a $C_6$-$C_{14}$ arylene group; and E independently represents a group chosen from —O—$R_3$—O—, —S—$R_4$—S—, or —$R_5$—N($R_6$)—$R_4$—N($R_6$)—$R_5$—, wherein:

—$R_3$ and $R_4$ independently represent a divalent hydrocarbon-based radical, optionally interrupted with one or more heteroatoms;

—$R_5$ independently represents a covalent bond or a saturated divalent hydrocarbon-based radical, optionally interrupted with one or more heteroatoms; and —$R_6$ independently represents a hydrogen atom or a hydrocarbon-based radical, optionally interrupted with one or more heteroatoms, and b) at least one coloring agent chosen from pigments, direct dyes, or mixtures of two or more thereof.

2. The composition for dyeing hair according to claim 1, wherein the at least one (poly)carbodiimide compound is chosen from compounds of formula (I) wherein:

$X_1$ and $X_2$ each represent an oxygen atom;

$R_1$ and $R_2$ are independently chosen from dialkylamino alcohols, alkyl esters of hydroxycarboxylic acid, or monoalkyl ethers of (poly)alkylene glycol in which a hydroxyl group has been removed;

n and z independently denote an integer ranging from 1 to 20;

w is equal to 1;

$L_1$ is independently chosen from a $C_1$-$C_{18}$ divalent aliphatic hydrocarbon-based radical, a $C_3$-$C_{15}$ cycloalkylene radical, a $C_3$-$C_{12}$ heterocycloalkylene group, or a $C_6$-$C_{14}$ arylene group; and E independently represents a group chosen from —O—$R_3$—O—, —S—$R_4$—S—, or —$R_5$—N($R_6$)—$R_4$—N($R_6$)—$R_5$—, wherein:

$R_3$ and $R_4$ are independently chosen from a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms;

$R_5$ is independently chosen from a covalent bond, a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms; and $R_6$ is independently chosen from a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms.

3. The composition for dyeing hair according to claim 1, wherein the at least one (poly)carbodiimide compound is chosen from compounds of formula (I) wherein:

$X_1$ and $X_2$ each represent an oxygen atom;

$R_1$ and $R_2$ are independently chosen from monoalkyl ethers of (poly)alkylene glycol in which a hydroxyl group has been removed;

n and z independently denote an integer ranging from 1 to 20;

w is equal to 1;

$L_1$ is a $C_3$-$C_{15}$ cycloalkylene radical; and

E independently represents a group chosen from —O—$R_3$—O—, —S—$R_4$—S—, or —$R_5$—N($R_6$)—$R_4$—N($R_6$)—$R_5$—, wherein:

$R_3$ and $R_4$ are independently chosen from a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms;

$R_5$ is independently chosen from a covalent bond, a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms; and $R_6$ is independently chosen from a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms.

4. The composition for dyeing hair according to claim 1, wherein the at least one (poly)carbodiimide compound is chosen from compounds of formula (I) wherein:

$X_1$ and $X_2$ each represent an oxygen atom;

$R_1$ and $R_2$ independently represent the compound of formula (V) below:

$$R_{13}\text{—}[O\text{—}CH_2\text{—}C(H)(R_{14})]_q\text{—} \quad (V)$$

wherein $R_{13}$ represents a $C_1$-$C_4$ alkyl group or a phenyl group, $R_{14}$ represents a hydrogen atom or a $C_1$-$C_4$ alkyl group, and q denotes an integer ranging from 4 to 30;

n and z independently denote an integer ranging from 2 to 20, with n+z ranging from 4 to 10;

w is equal to 1;

$L_1$ is a $C_3$-$C_{15}$ cycloalkylene radical, and

E represents a group —O—$R_3$—O—, wherein $R_3$ is chosen from a $C_6$-$C_{14}$ arylene radical, a $C_3$-$C_{12}$ cycloalkylene radical, or a linear or branched $C_1$-$C_{18}$ alkylene radical, optionally interrupted with one or more heteroatoms.

5. The composition for dyeing hair according to claim 1, wherein the at least one (poly)carbodiimide compound is chosen from compounds of formula (I) wherein:

$X_1$ and $X_2$ each represent an oxygen atom;

$R_1$ and $R_2$ independently represent the compound of formula (V) below:

$$R_{13}—[O—CH_2—C(H)(R_{14})]_q— \quad (V)$$

wherein $R_{13}$ represents a $C_1$-$C_4$ alkyl group or a phenyl group, $R_{14}$ represents a hydrogen atom or a $C_1$-$C_4$ alkyl group, and q denotes an integer ranging from 4 to 30;

n and z independently denote an integer ranging from 2 to 20, with n+z ranging from 4 to 10;

w is equal to 1;

$L_1$ is a $C_3$-$C_{15}$ cycloalkylene radical, and

E independently represents a group —O—$R_3$—O—, wherein $R_3$ represents a linear or branched $C_1$-$C_{18}$ alkylene radical, optionally interrupted with one or more heteroatoms.

6. The composition for dyeing hair according to claim 1, wherein the at least one (poly)carbodiimide compound is chosen from compounds of formula (XI) below:

(XI)

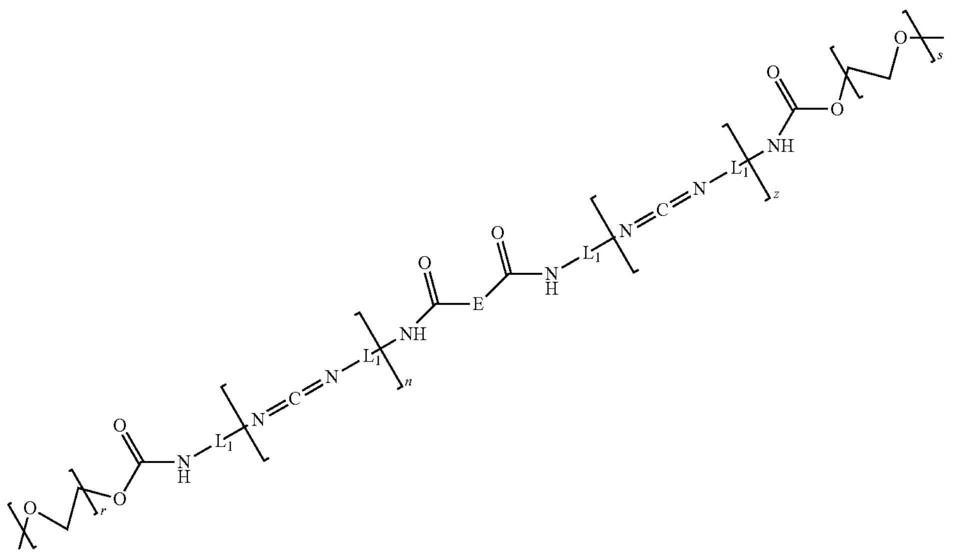

wherein $L_1$ is 4,4-dicyclohexylenemethane;

n and z independently denote an integer ranging from 1 to 20;

r and s independently denote an integer ranging from 4 to 30; and

E represents a group —O—$R_3$—O—, wherein $R_3$ represents a linear or branched $C_1$-$C_{18}$ alkylene radical, optionally interrupted with one or more heteroatoms.

7. The composition for dyeing hair according to claim 1, wherein the total amount of (poly)carbodiimide compounds of formula (I) ranges from 0.01% to 40% by weight, relative to the total weight of the composition.

8. The composition for dyeing hair according to claim 1, further comprising at least one aqueous dispersion of particles of polymers chosen from polyurethane polymers, acrylic polymers, or mixtures of two or more thereof.

9. The composition for dyeing hair according to claim 8, wherein the at least one aqueous dispersion of particles of polymers is chosen from aqueous dispersions of film-forming acrylic polymer particles.

10. The composition for dyeing hair according to claim 8, comprising at least one aqueous dispersion of acrylic polymer particles, wherein the acrylic polymer comprises one or more units derived from the following monomers:

a) (meth)acrylic acid; or b) $C_1$-$C_{30}$ alkyl (meth)acrylate.

11. The composition for dyeing hair according to claim 8, wherein the aqueous dispersion of polymer particles is present in the composition in an amount ranging from 0.1% to 40% by weight, relative to the total weight of the composition.

12. The composition for dyeing hair according to claim 8, wherein the aqueous dispersion has a solids content of polymer particles ranging from 20% to 60% by weight, relative to the total weight of the aqueous dispersion.

13. The composition for dyeing hair according to claim 1, further comprising at least one silicone.

14. The composition for dyeing hair according to claim 13, wherein the at least one silicone is chosen from non-amino silicones, amino silicones, or mixtures of two or more thereof.

15. The composition for dyeing hair according to claim 13, wherein the total amount of silicones ranges from 0.01% to 20% by weight, relative to the total weight of the composition.

16. A method for dyeing hair comprising applying to the hair a composition comprising:
   a) at least one (poly)carbodiimide compound chosen from compounds of formula (I) below:

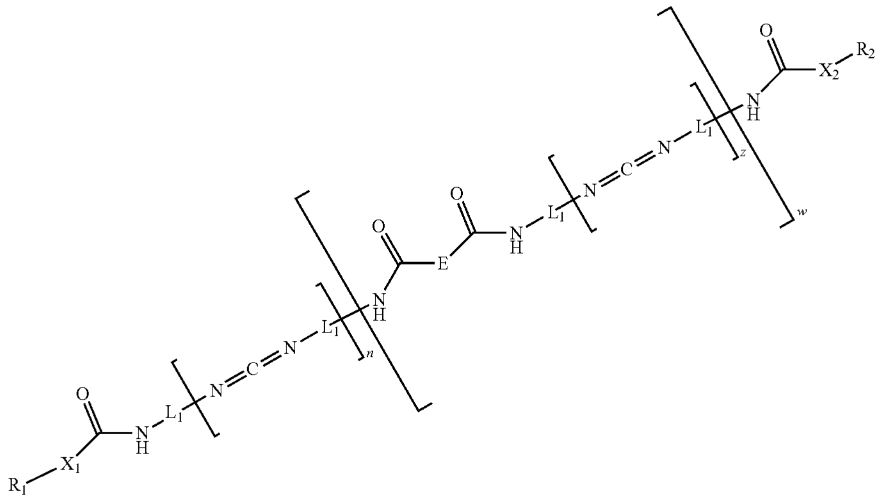

wherein:
   $X_1$ and $X_2$ independently represent an oxygen atom, a sulfur atom, or an —NH group;
   $R_1$ and $R_2$ independently represent a hydrocarbon-based radical, optionally interrupted with one or more heteroatoms;
   n and z independently denote an integer ranging from 1 to 20;
   w denotes an integer ranging from 1 to 3;
   $L_1$ independently represents a $C_1$-$C_{18}$ divalent aliphatic hydrocarbon-based radical, a $C_3$-$C_{15}$ cycloalkylene radical, a $C_3$-$C_{12}$ heterocycloalkylene group, or a $C_6$-$C_{14}$ arylene group; and
   E independently represents a group chosen from —O—$R_3$—O—, —S—$R_4$—S—, or —$R_5$—N($R_6$)—$R_4$—N($R_6$)—$R_5$—, wherein:
   $R_3$ and $R_4$ independently represent a divalent hydrocarbon-based radical, optionally interrupted with one or more heteroatoms;
   $R_5$ independently represents a covalent bond or a saturated divalent hydrocarbon-based radical, optionally interrupted with one or more heteroatoms; and
   $R_6$ independently represents a hydrogen atom or a hydrocarbon-based radical, optionally interrupted with one or more heteroatoms, and
   b) at least one coloring agent chosen from pigments, direct dyes, or mixtures thereof.

17. The method for dyeing hair according to claim 16, further comprising applying heat to the hair.

18. The method for dyeing hair according to claim 17, wherein applying heat comprises exposing the hair to a temperature ranging from 30° C. to 110° C.

19. The method for dyeing hair according to claim 17, wherein applying heat comprises exposing the hair to a temperature ranging from 110° C. to 220° C.

20. A kit for altering the color of hair comprising:
   (i) a first compartment comprising first composition comprising at least one (poly)carbodiimide compound chosen from compounds of formula (I):

(I)

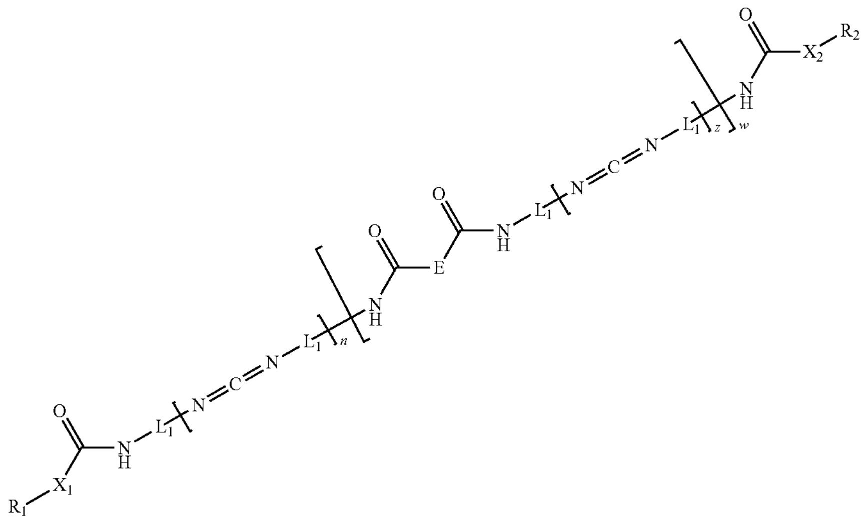

wherein:

$X_1$ and $X_2$ independently represent an oxygen atom, a sulfur atom, or an —NH group;

$R_1$ and $R_2$ independently represent a hydrocarbon-based radical, optionally interrupted with one or more heteroatoms;

n and z independently denote an integer ranging from 1 to 20;

w denotes an integer ranging from 1 to 3;

$L_1$ independently represents a $C_1$-$C_{18}$ divalent aliphatic hydrocarbon-based radical, a $C_3$-$C_{15}$ cycloalkylene radical, a $C_3$-$C_{12}$ heterocycloalkylene group, or a $C_6$-$C_{14}$ arylene group; and E independently represents a group chosen from —O—$R_3$—O—, —S—$R_4$—S—, or —$R_5$—N($R_6$)—$R_4$—N($R_6$)—$R_5$—, wherein:

$R_3$ and $R_4$ independently represent a divalent hydrocarbon-based radical, optionally interrupted with one or more heteroatoms;

$R_5$ independently represents a covalent bond or a saturated divalent hydrocarbon-based radical, optionally interrupted with one or more heteroatoms; and $R_6$ independently represents a hydrogen atom or a hydrocarbon-based radical, optionally interrupted with one or more heteroatoms, and (ii) a second compartment comprising a second composition comprising at least one aqueous dispersion of particles of polymers chosen from polyurethanes, acrylic polymers, or mixtures thereof;

wherein at least one of the first and second compositions comprises a coloring agent chosen from pigments, direct dyes, or mixtures thereof.

* * * * *